(12) United States Patent
Hornik et al.

(10) Patent No.: US 6,841,533 B1
(45) Date of Patent: Jan. 11, 2005

(54) CONFORMATIONALLY CONSTRAINED BACKBONE CYCLIZED INTERLEUKIN-6 ANTAGONISTS

(75) Inventors: Vered Hornik, Rehovot (IL); Eran Hadas, Rishon Lezion (IL)

(73) Assignee: Peptor Limited, Rehovot (IL)

( * ) Notice: Subject to any disclaimer, the term of this patent is extended or adjusted under 35 U.S.C. 154(b) by 0 days.

(21) Appl. No.: 09/644,456

(22) Filed: Aug. 24, 2000

Related U.S. Application Data

(63) Continuation of application No. PCT/IL00/00305, filed on May 28, 2000, and a continuation of application No. 09/434,025, filed on Nov. 4, 1999, now abandoned, which is a continuation-in-part of application No. 08/569,042, filed on Dec. 7, 1995, now Pat. No. 6,117,974.

(30) Foreign Application Priority Data

Jun. 1, 1999 (IL) .................................................. 130238

(51) Int. Cl.$^7$ ........................ A61K 38/12; A61K 38/07; C07K 5/10; C07K 5/12

(52) U.S. Cl. .......................... 514/9; 530/317; 530/330; 514/11; 514/18

(58) Field of Search .............................. 514/9, 18, 17; 530/317, 330

(56) References Cited

U.S. PATENT DOCUMENTS

| | | | |
|---|---|---|---|
| 3,988,304 A | 10/1976 | Garsky | 260/78 A |
| 4,011,182 A | 3/1977 | Sarantakis | 260/8 |
| 4,054,558 A | 10/1977 | Garsky | 260/112.5 S |
| 4,187,217 A | 2/1980 | Chipens et al. | 260/112.5 R |
| 4,235,886 A * | 11/1980 | Freidinger et al. | 424/177 |
| 4,310,518 A | 1/1982 | Freidinger et al. | 424/177 |
| 5,210,075 A | 5/1993 | Scholz et al. | 514/14 |
| 5,364,851 A | 11/1994 | Joran | 530/345 |
| 5,371,070 A | 12/1994 | Koerber et al. | 514/9 |
| 5,420,109 A | 5/1995 | Suto et al. | 514/8 |
| 5,470,942 A | 11/1995 | Alexander et al. | 528/328 |
| 5,639,455 A | 6/1997 | Shimamura et al. | 424/133.1 |
| 5,770,687 A | 6/1998 | Hornik et al. | 530/311 |
| 5,874,529 A | 2/1999 | Gilon et al. | 530/317 |
| 5,883,293 A | 3/1999 | Gilon et al. | 562/455 |
| 6,051,554 A | 4/2000 | Hornik et al. | 514/11 |

FOREIGN PATENT DOCUMENTS

| | | |
|---|---|---|
| DE | 41 19 544 C1 | 10/1992 |
| DE | 41 19 544 | 11/1992 |
| EP | 031 303 | 7/1981 |
| EP | 0 031 303 | 7/1981 |
| EP | 334 244 | 9/1989 |
| EP | 0 334 244 A2 | 9/1989 |
| EP | 336 779 | 10/1989 |
| EP | 0 336 779 A2 | 10/1989 |
| EP | 0 370 453 B1 | 5/1990 |
| EP | 370 453 | 5/1990 |
| EP | 395 417 | 10/1990 |
| EP | 0 395 417 | 10/1990 |
| EP | 0 336 779 A3 | 8/1991 |
| EP | 564 739 | 10/1993 |
| EP | 0 564 739 A2 | 10/1993 |
| EP | 0 564 739 A3 | 4/1995 |
| FR | 2 304 352 | 10/1976 |
| FR | 2411828 | 7/1979 |
| FR | 2 411 828 | 7/1979 |
| WO | WO 89/01781 | 3/1989 |
| WO | WO 92/00091 | 1/1992 |
| WO | WO 92/22566 | 12/1992 |
| WO | WO 93/01206 | 1/1993 |
| WO | WO 94/11393 | 5/1994 |
| WO | WO 95/01800 | 1/1995 |
| WO | WO 95/13086 | 5/1995 |
| WO | WO 95/33765 | 12/1995 |
| WO | WO 97/09344 | 3/1997 |
| WO | WO 97/13781 | 4/1997 |
| WO | WO 97/48728 | 12/1997 |
| WO | WO 98/04583 | 2/1998 |
| WO | WO 99/65508 | 12/1999 |
| WO | WO 00/72864 A1 | 7/2000 |

OTHER PUBLICATIONS

Bell et al., 1993, "Molecular biology of somatostatin receptors", *TINS* 16:34–38.

Brazeau et al. 1973, "Hypothalamic Polypeptide That Inhibits the Secretion of Immunoreactive Pituitary Growth Hormone", *Science* 179:77–79.

Buscail et al., 1995, "Inhibition of cell proliferation by the somatostatin analogue RC–160 is mediated mechanisms", *Proc. Natl.* by somatostatin receptor subtypes SSTR2 and SSTR5 through different *Acad. Sci. USA* 92:1580–1584.

Hirano, T., 1998, "*Interleukin 6 and its Receptor: Ten Years Later*", Intern. Rev. Immunol., 16:249.

Yoshizaki et al., 1998, "*Therapy of Rheumatoid Arthritis by Blocking IL–6 Signal Transduction with a Humanized Anti–IL–6 Receptor Antibody*", Springer Semin. Immunopathol., 20: 247.

Kozak et al., 1997, "*Sickness Behavior in Mice Deficient in Interleukin–6 During Turpentine Abscess and Influenza Pneumonitis*", American J. Physiology, 272: 2 R621.

Simpson et al., 1997, "*Interleukin–6: Structure–function Relationships*", Protein Sci., 6: 929.

Xu et al., 1997, "*Solution Structure of Recombinant Human Interleukin–6*", J. Mol. Biol., 268: 468.

(List continued on next page.)

*Primary Examiner*—Michael Borin
(74) *Attorney, Agent, or Firm*—Winston & Strawn LLP

(57) ABSTRACT

Novel peptides which are conformationally constrained backbone cyclized antagonists of IL-6, are disclosed. Methods for synthesizing the IL-6 antagonists are also disclosed. Furthermore, pharmaceutical compositions comprising IL-6 antagonists, and methods of using such compositions are disclosed.

2 Claims, 4 Drawing Sheets

OTHER PUBLICATIONS

Fourcin et al., 1996, "gp130 Transducing Receptor Cross–linking Is Sufficient to Induce Interleukin–6 Type Responses", J. Biol. Chem., 271: 11756.

Murakamin–Mori et al., 1996, "The Soluble Form of the IL–6 Receptor (sIL–6Rα) Is a Potent Growth Factor for AIDS–associated Kaposi's sarcoma (KS) cells; the Soluble Form of gp130 is Antagonistic for sIL–6Rα–Induced AIDS–KS Cell Growth", Int. Immunol., 8: 595.

Ogata, A., 1996, "Therapeutic Strategies of Inhibition of Interleukin–6 Mediated Multiple Myeloma Cell Growth", Leuk. Res., 20: 303.

Sporeno et al., 1996, "Human Interleukin–6 Receptor Super–Antagonists with High Potency and Wide Spectrum on Multiple Myeloma Cells", Blood, 87: 4510.

Toniatti et al., 1996, "Engineering Human Interleukin–6 to Obtain Variants with Strongly Enhanced Bioactivity", The EMBO J., 15: 2726.

Halimi et al., 1995, "Epitope Peptides from Interleukin–6 Receptor Which Inhibit the Growth of Human Myeloma Cells", Eur. Cytokin. Netw., 6: 135.

Klein et al., 1995, "Interleukin–6 in Human Multiple Myeloma", Blood, 85:863.

Byk et al., 1992, "Building units for N–backbone cyclic peptides. 1. Synthesis of protected N–(ω–aminoalkylene)amino acids and their incorporation into dipeptide units", J. Org. Chem. 57:5687–5692.

Charpentier et al., 1989, "Synthesis and binding affinities of cyclic and related linear analogues of $CCK_B$ selective for central receptors," J. Med. Chem, pp. 1184–1190.

Giannis et al., 1993, "Peptidomimetics for receptor ligands—discovery, development, and medical perspective," Angew. Chem. Int. Ed. Engl. 32: 1244–1267.

Gilon et al., 1991, "Backbone Cyclization: A New Method for Conferring Conformational Constraint on Peptides", Biopolymers 31:745–750.

Gilon et al., 1992, "SAR studies of cycloseptide: effects of cyclization and charge at position 6," Chem. Biol. Proc. Am. Pept. Symp 1th. pp. 476–477.

Greiner et al., 1994, "Synthesis of New Backbone–Cyclized Bradykinin Analogs", Proc. Eur. Pept. Symp., 23rd, Meeting Date 1994, 289–290.

Hruby et al., 1990, "Emerging approaches in the molecular design of receptor–selective peptide ligands: conformational, topographical and dynamic considerations," Biochem. J. 268: 249–262.

Klein, et al., 1995, "Interleukin–6 in Human Multiple Myeloma," Blood, vol. 85, No. 4, pp. 863–872.

Krstenansky et al., 1994, "Cyclic hexapeptide antagonists of the bradykinin $B_2$ receptor: Receptor binding and solution backbone conformation", Letters in Peptide Science 1:229–234.

Lamberts, 1988, "The role of Somastatin in the regulation of anterior pituitary hormone secretion and the use of its analogs in the treatment of human pituitary tumors," Endocrine Reviews vol. 9, No. 4, pp. 417–436.

Lamberts et al., 1990,"Somastatin–receptor imaging in the localization of endocrine tumors," New England J. Med. 323: 1246–1249.

Lymangrover et al., 1993, "Varying the duration of A23187 administration alters its effect on adrenal steroidogenesis," Life sciences 34:371–377.

Mosberg et al., 1983, "Bis–penicillamine enkephalins posses highly improved specificity toward δ opioid receptors," Biochemistry 80:5871–5874.

Plotsky et al., 1985, "Patterns of growth hormone–releasing factor and somatostatin secretion into the hypophysial–portal circulation of the rat," Science 230:461–463.

Raynor et al., 1993, "Cloned somatostatin receptors: identification of subtype–selective peptides and demonstration of high affinity binding of linear peptides," Mol. pharmacol. 43:838–844.

Reisine et al., 1995, "Molecular biology of somatostatin receptors," Endocrine reviews 16, 427–442.

Reubi et al., 1995, "Multiple actions of somatostatin in neoplastic disease," TIPS 16:110–115.

Rizo et al., 1992, "Constrained peptides: Models of bioactive peptides and protein substructures," Annu. Rev. Biochem. 61:387–418.

Rodriguez et al. 1990, "Synthesis of cyclic analogues of cholecystokinin highly selective for central receptors," Int. J. Peptide Protein Res. 35:441–451.

Rudinger, 1976, "Characteristics of the Amino Acids as components of a peptide hormone sequence," Peptide Hormones, Ed. J.A. Parsons, University Park Press, Baltimore, pp. 1–7.

Schumann et al., 1996, Database Caplus, DN: 130:14228. Pept. 1996, Proc. Eur. Pept. Symp., 24th (1998). Meeting Date 1996, 797–798. Editors: Ramage, Robert; Epton, Roger. Publisher: Mayflower Scientific, Kingswinford, UK.

Steranka et al., 1988, "Bradykinin as a pain mediator: receptors are localized to sensory neurons, and antagonists have analgesic actions," Proc. Natl. Acad. Sci. USA 85:3245–3249.

Verber et al., 1984, "A super active cyclic hexapeptide analog of somatostatin," Life sciences 34:1371–1378.

Verber et al., 1985, "The design of metabolically–stable peptide analogs," TINS, pp. 392–396.

Zuckerman, 1993, "The chemical synthesis of peptidomimetic libraries," Current Opinion in Structure Biol., 3: 580–584.

* cited by examiner

SEQUENCE LISTING

<160> NUMBER OF SEQ ID NOS: 83

<210> SEQ ID NO 1
<211> LENGTH: 9
<212> TYPE: PRT
<213> ORGANISM: Homo sapiens

<400> SEQUENCE: 1

Trp Arg Leu Arg Phe Ala Leu Tyr Ala
 1               5

<210> SEQ ID NO 2
<211> LENGTH: 9

```
<212> TYPE: PRT
<213> ORGANISM: Homo sapiens

<400> SEQUENCE: 2

Lys Arg Leu Arg Phe Ala Leu Tyr Ala
 1               5

<210> SEQ ID NO 3
<211> LENGTH: 9
<212> TYPE: PRT
<213> ORGANISM: Homo sapiens

<400> SEQUENCE: 3

Tyr Arg Leu Arg Phe Ala Leu Tyr Ala
 1               5

<210> SEQ ID NO 4
<211> LENGTH: 9
<212> TYPE: PRT
<213> ORGANISM: Homo sapiens

<400> SEQUENCE: 4

Phe Arg Leu Arg Phe Ala Leu Tyr Ala
 1               5

<210> SEQ ID NO 5
<211> LENGTH: 9
<212> TYPE: PRT
<213> ORGANISM: Homo sapiens

<400> SEQUENCE: 5

Trp Arg Leu Arg Phe Ala Lys Tyr Ala
 1               5

<210> SEQ ID NO 6
<211> LENGTH: 9
<212> TYPE: PRT
<213> ORGANISM: Homo sapiens

<400> SEQUENCE: 6

Lys Arg Leu Arg Phe Ala Lys Tyr Ala
 1               5

<210> SEQ ID NO 7
<211> LENGTH: 9
<212> TYPE: PRT
<213> ORGANISM: Homo sapiens

<400> SEQUENCE: 7

Tyr Arg Leu Arg Phe Ala Lys Tyr Ala
 1               5

<210> SEQ ID NO 8
<211> LENGTH: 9
<212> TYPE: PRT
<213> ORGANISM: Homo sapiens

<400> SEQUENCE: 8

Phe Arg Leu Arg Phe Ala Lys Tyr Ala
 1               5

<210> SEQ ID NO 9
<211> LENGTH: 9
<212> TYPE: PRT
<213> ORGANISM: Homo sapiens
```

```
<400> SEQUENCE: 9

Trp Arg Lys Arg Phe Ala Leu Tyr Ala
 1               5

<210> SEQ ID NO 10
<211> LENGTH: 9
<212> TYPE: PRT
<213> ORGANISM: Homo sapiens

<400> SEQUENCE: 10

Lys Arg Lys Arg Phe Ala Leu Tyr Ala
 1               5

<210> SEQ ID NO 11
<211> LENGTH: 9
<212> TYPE: PRT
<213> ORGANISM: Homo sapiens

<400> SEQUENCE: 11

Tyr Arg Lys Arg Phe Ala Leu Tyr Ala
 1               5

<210> SEQ ID NO 12
<211> LENGTH: 9
<212> TYPE: PRT
<213> ORGANISM: Homo sapiens

<400> SEQUENCE: 12

Phe Arg Lys Arg Phe Ala Leu Tyr Ala
 1               5

<210> SEQ ID NO 13
<211> LENGTH: 9
<212> TYPE: PRT
<213> ORGANISM: Homo sapiens

<400> SEQUENCE: 13

Trp Arg Lys Arg Phe Ala Lys Tyr Ala
 1               5

<210> SEQ ID NO 14
<211> LENGTH: 9
<212> TYPE: PRT
<213> ORGANISM: Homo sapiens

<400> SEQUENCE: 14

Lys Arg Lys Arg Phe Ala Lys Tyr Ala
 1               5

<210> SEQ ID NO 15
<211> LENGTH: 9
<212> TYPE: PRT
<213> ORGANISM: Homo sapiens

<400> SEQUENCE: 15

Tyr Arg Lys Arg Phe Ala Lys Tyr Ala
 1               5

<210> SEQ ID NO 16
<211> LENGTH: 9
<212> TYPE: PRT
<213> ORGANISM: Homo sapiens

<400> SEQUENCE: 16
```

Phe Arg Lys Arg Phe Ala Lys Tyr Ala
 1               5

<210> SEQ ID NO 17
<211> LENGTH: 10
<212> TYPE: PRT
<213> ORGANISM: Homo sapiens

<400> SEQUENCE: 17

Trp Arg Leu Arg Phe Ala Leu Arg Tyr Ala
 1               5                  10

<210> SEQ ID NO 18
<211> LENGTH: 10
<212> TYPE: PRT
<213> ORGANISM: Homo sapiens

<400> SEQUENCE: 18

Lys Arg Leu Arg Phe Ala Leu Arg Tyr Ala
 1               5                  10

<210> SEQ ID NO 19
<211> LENGTH: 10
<212> TYPE: PRT
<213> ORGANISM: Homo sapiens

<400> SEQUENCE: 19

Tyr Arg Leu Arg Phe Ala Leu Arg Tyr Ala
 1               5                  10

<210> SEQ ID NO 20
<211> LENGTH: 10
<212> TYPE: PRT
<213> ORGANISM: Homo sapiens

<400> SEQUENCE: 20

Phe Arg Leu Arg Phe Ala Leu Arg Tyr Ala
 1               5                  10

<210> SEQ ID NO 21
<211> LENGTH: 10
<212> TYPE: PRT
<213> ORGANISM: Homo sapiens

<400> SEQUENCE: 21

Trp Arg Leu Arg Phe Ala Lys Arg Tyr Ala
 1               5                  10

<210> SEQ ID NO 22
<211> LENGTH: 10
<212> TYPE: PRT
<213> ORGANISM: Homo sapiens

<400> SEQUENCE: 22

Lys Arg Leu Arg Phe Ala Lys Arg Tyr Ala
 1               5                  10

<210> SEQ ID NO 23
<211> LENGTH: 10
<212> TYPE: PRT
<213> ORGANISM: Homo sapiens

<400> SEQUENCE: 23

Tyr Arg Leu Arg Phe Ala Lys Arg Tyr Ala

```
                        1               5              10

<210> SEQ ID NO 24
<211> LENGTH: 10
<212> TYPE: PRT
<213> ORGANISM: Homo sapiens

<400> SEQUENCE: 24

Phe Arg Leu Arg Phe Ala Lys Arg Tyr Ala
 1               5                  10

<210> SEQ ID NO 25
<211> LENGTH: 10
<212> TYPE: PRT
<213> ORGANISM: Homo sapiens

<400> SEQUENCE: 25

Trp Arg Lys Arg Phe Ala Leu Arg Tyr Ala
 1               5                  10

<210> SEQ ID NO 26
<211> LENGTH: 10
<212> TYPE: PRT
<213> ORGANISM: Homo sapiens

<400> SEQUENCE: 26

Lys Arg Lys Arg Phe Ala Leu Arg Tyr Ala
 1               5                  10

<210> SEQ ID NO 27
<211> LENGTH: 10
<212> TYPE: PRT
<213> ORGANISM: Homo sapiens

<400> SEQUENCE: 27

Tyr Arg Lys Arg Phe Ala Leu Arg Tyr Ala
 1               5                  10

<210> SEQ ID NO 28
<211> LENGTH: 10
<212> TYPE: PRT
<213> ORGANISM: Homo sapiens

<400> SEQUENCE: 28

Phe Arg Lys Arg Phe Ala Leu Arg Tyr Ala
 1               5                  10

<210> SEQ ID NO 29
<211> LENGTH: 10
<212> TYPE: PRT
<213> ORGANISM: Homo sapiens

<400> SEQUENCE: 29

Trp Arg Lys Arg Phe Ala Lys Arg Tyr Ala
 1               5                  10

<210> SEQ ID NO 30
<211> LENGTH: 10
<212> TYPE: PRT
<213> ORGANISM: Homo sapiens

<400> SEQUENCE: 30

Lys Arg Lys Arg Phe Ala Lys Arg Tyr Ala
 1               5                  10
```

```
<210> SEQ ID NO 31
<211> LENGTH: 10
<212> TYPE: PRT
<213> ORGANISM: Homo sapiens

<400> SEQUENCE: 31

Tyr Arg Lys Arg Phe Ala Lys Arg Tyr Ala
1               5                   10

<210> SEQ ID NO 32
<211> LENGTH: 10
<212> TYPE: PRT
<213> ORGANISM: Homo sapiens

<400> SEQUENCE: 32

Phe Arg Lys Arg Phe Ala Lys Arg Tyr Ala
1               5                   10

<210> SEQ ID NO 33
<211> LENGTH: 10
<212> TYPE: PRT
<213> ORGANISM: Homo sapiens

<400> SEQUENCE: 33

Lys Gly Leu Ile Gln Leu Phe Gly Lys Lys
1               5                   10

<210> SEQ ID NO 34
<211> LENGTH: 11
<212> TYPE: PRT
<213> ORGANISM: Homo sapiens

<400> SEQUENCE: 34

Thr Gly Gln Gly Ala Ala Ile Ile Gly Gln Pro
1               5                   10

<210> SEQ ID NO 35
<211> LENGTH: 10
<212> TYPE: PRT
<213> ORGANISM: Homo sapiens

<400> SEQUENCE: 35

Tyr Arg Leu Arg Phe Gly Leu Arg Tyr Gly
1               5                   10

<210> SEQ ID NO 36
<211> LENGTH: 10
<212> TYPE: PRT
<213> ORGANISM: Homo sapiens

<400> SEQUENCE: 36

Tyr Arg Leu Arg Phe Gly Leu Arg Gly Arg
1               5                   10

<210> SEQ ID NO 37
<211> LENGTH: 10
<212> TYPE: PRT
<213> ORGANISM: Homo sapiens

<400> SEQUENCE: 37

Gly Glu Ser Gln Lys Gly Ala Ala Gln Leu
1               5                   10

<210> SEQ ID NO 38
```

-continued

```
<211> LENGTH: 10
<212> TYPE: PRT
<213> ORGANISM: Homo sapiens

<400> SEQUENCE: 38

Tyr Arg Leu Arg Phe Glu Gly Arg Tyr Gly
1               5                   10

<210> SEQ ID NO 39
<211> LENGTH: 10
<212> TYPE: PRT
<213> ORGANISM: Homo sapiens

<400> SEQUENCE: 39

Arg Leu Arg Ala Glu Gly Ser Lys Gly Phe
1               5                   10

<210> SEQ ID NO 40
<211> LENGTH: 11
<212> TYPE: PRT
<213> ORGANISM: Homo sapiens

<400> SEQUENCE: 40

Asp Leu Gln Gly Ser Leu Arg Ala Leu Arg Gln
1               5                   10

<210> SEQ ID NO 41
<211> LENGTH: 10
<212> TYPE: PRT
<213> ORGANISM: Homo sapiens

<400> SEQUENCE: 41

Tyr Arg Leu Phe Arg Gly Leu Arg Tyr Gly
1               5                   10

<210> SEQ ID NO 42
<211> LENGTH: 10
<212> TYPE: PRT
<213> ORGANISM: Homo sapiens

<400> SEQUENCE: 42

Tyr Arg Lys Arg Phe Gly Leu Arg Gly Arg
1               5                   10

<210> SEQ ID NO 43
<211> LENGTH: 10
<212> TYPE: PRT
<213> ORGANISM: Homo sapiens

<400> SEQUENCE: 43

Tyr Arg Gly Arg Phe Glu Leu Arg Gly Arg
1               5                   10

<210> SEQ ID NO 44
<211> LENGTH: 12
<212> TYPE: PRT
<213> ORGANISM: Homo sapiens

<400> SEQUENCE: 44

Tyr Arg Leu Arg Phe Ala Leu Arg Tyr Ala Ala Glu
1               5                   10

<210> SEQ ID NO 45
<211> LENGTH: 10
<212> TYPE: PRT
```

<213> ORGANISM: Homo sapiens

<400> SEQUENCE: 45

Phe Arg Leu Arg Phe Ala Leu Arg Tyr Ala
 1               5                  10

<210> SEQ ID NO 46
<211> LENGTH: 10
<212> TYPE: PRT
<213> ORGANISM: Homo sapiens

<400> SEQUENCE: 46

Tyr Arg Leu Arg Phe Gly Leu Arg Tyr Gly
 1               5                  10

<210> SEQ ID NO 47
<211> LENGTH: 11
<212> TYPE: PRT
<213> ORGANISM: Homo sapiens

<400> SEQUENCE: 47

Leu Tyr Arg Leu Arg Phe Gly Leu Arg Gly Arg
 1               5                  10

<210> SEQ ID NO 48
<211> LENGTH: 10
<212> TYPE: PRT
<213> ORGANISM: Homo sapiens

<400> SEQUENCE: 48

Arg Tyr Arg Ala Glu Gly Ser Lys Gly Phe
 1               5                  10

<210> SEQ ID NO 49
<211> LENGTH: 11
<212> TYPE: PRT
<213> ORGANISM: Homo sapiens

<400> SEQUENCE: 49

Leu Ala Glu Arg Ser Lys Thr Phe Thr Thr Trp
 1               5                  10

<210> SEQ ID NO 50
<211> LENGTH: 10
<212> TYPE: PRT
<213> ORGANISM: Homo sapiens

<400> SEQUENCE: 50

Gly Arg Gly Lys Thr Phe Thr Thr Trp Met
 1               5                  10

<210> SEQ ID NO 51
<211> LENGTH: 10
<212> TYPE: PRT
<213> ORGANISM: Homo sapiens

<400> SEQUENCE: 51

Ala Gly Arg Phe Lys Thr Phe Thr Gly Trp
 1               5                  10

<210> SEQ ID NO 52
<211> LENGTH: 11
<212> TYPE: PRT
<213> ORGANISM: Homo sapiens

```
<400> SEQUENCE: 52

Leu Ala Val Ala Arg Gly Pro Arg Trp Leu Gly
1               5                   10

<210> SEQ ID NO 53
<211> LENGTH: 10
<212> TYPE: PRT
<213> ORGANISM: Homo sapiens

<400> SEQUENCE: 53

Ala Val Pro Glu Gly Asp Ser Gly Phe Ile
1               5                   10

<210> SEQ ID NO 54
<211> LENGTH: 10
<212> TYPE: PRT
<213> ORGANISM: Homo sapiens

<400> SEQUENCE: 54

Ala Val Pro Glu Gly Asp Ser Gly Tyr Ile
1               5                   10

<210> SEQ ID NO 55
<211> LENGTH: 10
<212> TYPE: PRT
<213> ORGANISM: Homo sapiens

<400> SEQUENCE: 55

Glu Gly Gly Ser Ser Phe Tyr Gly Val Ser
1               5                   10

<210> SEQ ID NO 56
<211> LENGTH: 10
<212> TYPE: PRT
<213> ORGANISM: Homo sapiens

<400> SEQUENCE: 56

Tyr Ile Val Ser Gly Ala Val Ala Ser Gly
1               5                   10

<210> SEQ ID NO 57
<211> LENGTH: 10
<212> TYPE: PRT
<213> ORGANISM: Homo sapiens

<400> SEQUENCE: 57

Gly Met Ala Val Ala Ser Ser Val Gly Gly
1               5                   10

<210> SEQ ID NO 58
<211> LENGTH: 10
<212> TYPE: PRT
<213> ORGANISM: Homo sapiens

<400> SEQUENCE: 58

Ala Val Gly Ser Ser Val Gly Gly Lys Phe
1               5                   10

<210> SEQ ID NO 59
<211> LENGTH: 10
<212> TYPE: PRT
<213> ORGANISM: Homo sapiens

<400> SEQUENCE: 59
```

```
Gly Ala Gly Ile Leu Gln Pro Gly Pro Pro
1               5                   10
```

<210> SEQ ID NO 60
<211> LENGTH: 10
<212> TYPE: PRT
<213> ORGANISM: Homo sapiens

<400> SEQUENCE: 60

```
Gly Gln Pro Asp Pro Pro Ala Gly Ile Thr
1               5                   10
```

<210> SEQ ID NO 61
<211> LENGTH: 10
<212> TYPE: PRT
<213> ORGANISM: Homo sapiens

<400> SEQUENCE: 61

```
Ser Gln Gly Ser Gln Lys Phe Ser Ala Gly
1               5                   10
```

<210> SEQ ID NO 62
<211> LENGTH: 10
<212> TYPE: PRT
<213> ORGANISM: Homo sapiens

<400> SEQUENCE: 62

```
Gly Asn Leu Pro Lys Met Ala Glu Lys Gly
1               5                   10
```

<210> SEQ ID NO 63
<211> LENGTH: 10
<212> TYPE: PRT
<213> ORGANISM: Homo sapiens

<400> SEQUENCE: 63

```
Gly Lys Val Leu Ile Gln Phe Gly Gln Lys
1               5                   10
```

<210> SEQ ID NO 64
<211> LENGTH: 10
<212> TYPE: PRT
<213> ORGANISM: Homo sapiens

<400> SEQUENCE: 64

```
Gly Asn Phe Thr Leu Lys Ser Gly Trp Ala
1               5                   10
```

<210> SEQ ID NO 65
<211> LENGTH: 10
<212> TYPE: PRT
<213> ORGANISM: Homo sapiens

<400> SEQUENCE: 65

```
Phe Ala Asp Ala Gly Ala Lys Arg Asp Gly
1               5                   10
```

<210> SEQ ID NO 66
<211> LENGTH: 10
<212> TYPE: PRT
<213> ORGANISM: Homo sapiens

<400> SEQUENCE: 66

```
Gly Thr Pro Thr Ser Ala Thr Gly Asp Tyr
1               5                   10
```

<210> SEQ ID NO 67
<211> LENGTH: 11
<212> TYPE: PRT
<213> ORGANISM: Homo sapiens

<400> SEQUENCE: 67

Leu Asn Phe Asp Pro Gly Tyr Lys Val Lys Gly
 1               5                  10

<210> SEQ ID NO 68
<211> LENGTH: 10
<212> TYPE: PRT
<213> ORGANISM: Homo sapiens

<400> SEQUENCE: 68

Asn Pro Gly His Asn Leu Ser Val Ile Gly
 1               5                  10

<210> SEQ ID NO 69
<211> LENGTH: 10
<212> TYPE: PRT
<213> ORGANISM: Homo sapiens

<400> SEQUENCE: 69

Ser Ile Gly Lys Leu Thr Trp Thr Asn Gly
 1               5                  10

<210> SEQ ID NO 70
<211> LENGTH: 10
<212> TYPE: PRT
<213> ORGANISM: Homo sapiens

<400> SEQUENCE: 70

Tyr Arg Gly Lys Asp Ala Ser Gly Trp Ser
 1               5                  10

<210> SEQ ID NO 71
<211> LENGTH: 10
<212> TYPE: PRT
<213> ORGANISM: Homo sapiens

<400> SEQUENCE: 71

Arg Thr Lys Asp Ala Ser Gly Trp Ser Gly
 1               5                  10

<210> SEQ ID NO 72
<211> LENGTH: 10
<212> TYPE: PRT
<213> ORGANISM: Homo sapiens

<400> SEQUENCE: 72

Gly Ile Pro Pro Glu Asp Thr Ala Ser Gly
 1               5                  10

<210> SEQ ID NO 73
<211> LENGTH: 10
<212> TYPE: PRT
<213> ORGANISM: Homo sapiens

<400> SEQUENCE: 73

Gly Asp Thr Ala Ser Thr Arg Ser Ser Gly
 1               5                  10

```
<210> SEQ ID NO 74
<211> LENGTH: 10
<212> TYPE: PRT
<213> ORGANISM: Homo sapiens

<400> SEQUENCE: 74

Gly Ala Ser Gly Arg Ser Ser Phe Thr Val
 1               5                  10

<210> SEQ ID NO 75
<211> LENGTH: 10
<212> TYPE: PRT
<213> ORGANISM: Homo sapiens

<400> SEQUENCE: 75

Ser Phe Gly Val Gln Asp Leu Lys Pro Gly
 1               5                  10

<210> SEQ ID NO 76
<211> LENGTH: 10
<212> TYPE: PRT
<213> ORGANISM: Homo sapiens

<400> SEQUENCE: 76

Tyr Val Phe Arg Ile Arg Gly Met Lys Gly
 1               5                  10

<210> SEQ ID NO 77
<211> LENGTH: 10
<212> TYPE: PRT
<213> ORGANISM: Homo sapiens

<400> SEQUENCE: 77

Lys Arg Lys Arg Phe Ala Leu Arg Tyr Ala
 1               5                  10

<210> SEQ ID NO 78
<211> LENGTH: 10
<212> TYPE: PRT
<213> ORGANISM: Homo sapiens

<400> SEQUENCE: 78

Trp Arg Lys Arg Phe Ala Leu Arg Tyr Ala
 1               5                  10

<210> SEQ ID NO 79
<211> LENGTH: 10
<212> TYPE: PRT
<213> ORGANISM: Homo sapiens

<400> SEQUENCE: 79

Lys Arg Leu Arg Phe Ala Leu Arg Tyr Ala
 1               5                  10

<210> SEQ ID NO 80
<211> LENGTH: 10
<212> TYPE: PRT
<213> ORGANISM: Homo sapiens

<400> SEQUENCE: 80

Lys Arg Lys Arg Phe Ala Lys Arg Tyr Ala
 1               5                  10

<210> SEQ ID NO 81
<211> LENGTH: 10
```

```
<212> TYPE: PRT
<213> ORGANISM: Homo sapiens

<400> SEQUENCE: 81

Tyr Arg Lys Arg Phe Ala Leu Arg Tyr Ala
 1               5                  10

<210> SEQ ID NO 82
<211> LENGTH: 10
<212> TYPE: PRT
<213> ORGANISM: Homo sapiens

<400> SEQUENCE: 82

Lys Arg Leu Arg Phe Ala Lys Arg Tyr Ala
 1               5                  10

<210> SEQ ID NO 83
<211> LENGTH: 6
<212> TYPE: PRT
<213> ORGANISM: homo sapiens
<220> FEATURE:
<221> NAME/KEY: misc_feature
<222> LOCATION: (4) .. (4)
<223> OTHER INFORMATION: ornithine

<400> SEQUENCE: 83

Lys Lys Ala Xaa Trp Phe
 1               5
```

CONFORMATIONALLY CONSTRAINED BACKBONE CYCLIZED INTERLEUKIN-6 ANTAGONISTS

CROSS REFERENCE TO RELATED APPLICATIONS

This application is a continuation of the U.S. national phase designation of international application No. PCT/IL00/00305 filed May 28, 2000, and is a continuation of U.S. application Ser. No. 09/434,025 filed Nov. 4, 1999 now abandoned, each of which is a continuation-in-part of U.S. application Ser. No. 08/569,042 filed Dec. 7, 1995 now U.S. Pat. No. 6,117,974.

FIELD OF THE INVENTION

The present invention relates to conformationally constrained backbone-cyclized IL-6 antagonists, and to pharmaceutical compositions containing same.

BACKGROUND OF THE INVENTION

Interleukin-6 (IL-6) is a member of the helical cytokine family. IL-6 is produced by almost all cell types in response to a variety of different stimuli including bacterial (LPS) and viral infections, cancer, and other cytokines (e.g. IL-1). IL-6 is a pleiotropic factor, it participates in numerous processes and is thus associated with numerous disorders (for a review see Hirano T., *Intern. Rev. Immunol.* 16:249, 1998).

Bioactivity of IL-6 requires interaction of the cytokine, IL-6, its receptor (IL-6R) and a transmembrane signal transducer known as glycoprotein 130 (gp130), and formation of a hexameric complex containing two units of each protein. The outcome of the complex formation is dimerization of gp130, which by itself is sufficient for obtaining IL-6 like bioactivity (Fourcin, et al., *J. Biol. Chem.* 271: 11756, 1996.). Several other cytokines also use gp130 for signal transduction. These include: interleukin-11 (IL-11), ciliary neurotrophic factor (CNTF), leukocyte inhibitory factor (LIF), oncostatin M (OSM).

IL-6 and Host Defense

IL-6 levels increases early during bacterial and viral infections. IL-6 induces production of acute phase proteins which are thought to participate in the defense of the host organism against tissue damage and infection. The acute phase response is considered to be the systemic inflammatory reaction to infection and injury.

IL-6 also amplifies the immune system through its multiple growth and differentiation activities such as induction of B cell differentiation, replication of bone marrow progenitor cells, and augmentation of T lymphocytes, including enhancement of cytotoxic T lymphocytes.

IL-6 in Homeostasis, Injury and Transplantation

IL-6 levels are increased during stress. IL-6 in rabbits is directly responsible for elevation of body temperature. High IL-6 levels in burn patients correlates with mortality. Elevated IL-6 levels are associated with traumatic events and allograft rejection.

IL-6 in Osteoporosis

Estrogen plays an important role in maintaining bone mass. A massive loss of bone mass is reported in women at there postmenopausal stage. Increased bone resorption and increased osteoclast activity in postmenopausal osteoporosis have been linked with IL-6. The production of IL-6 is elevated in bone marrow cells at this stage correlating the fact that estrogen down regulates IL-6 gene expression. Estrogen loss induced by ovariectomy in mice enhances osteoclast development and this change can be prevented by antibodies to IL-6. Several experiments including an IL-6 knockout mice model, treatment with anti IL-6 antibodies or with IL-6 antisense demonstrate that elevated levels of IL-6 plays a critical role in the formation of osteoclastic cells. As such, dysregulation of IL-6 activity in bone cells leads to the development of pathological disease.

IL-6 in Immune Disorders

Elevated levels of IL-6 in cardiac myxoma and cervical carcinoma are associated with autoimmunity indications such as: production of anti-nuclear factor, rheumatoid factors, elevated immune complexes, arthritis and nephritis.

Castelman's disease patients suffer form fever, anemia, hyper-γ-globulinemia, and an increase in acute phase proteins.

The lymph nodes constitutively produce large amounts of IL-6, and surgical removal of the involved lymph nodes is followed by decrease in serum IL-6 levels and a dramatic clinical improvement. It has been demonstrated that systemic manifestation of Castelman's disease could be alleviated by treatment with anti-IL-6 antibody.

Local and general symptoms of rheumatoid arthritis, such as plasma cell infiltration into synovial tissues, autoantibody production, and polyclonal hyper-γ-globulinemia can be explained by increased IL-6 production observed in synovial tissue. At least two mediators which are elevated in RA patients, PGE2 and IL-1, are known to induce synthesis of IL-6. Higher than normal levels of IL-6 have been detected in sera of patients with active SLE. Increased plasma levels of IL-6 were observed in psoriasis patients.

AIDS

High levels of IL-6 are associated with HIV infection. The HIV envelope glycoproteins gp120 and gp160 induce IL-6 production from CD4+ T cells. Is has been demonstrated that IL-6 is a growth factor of the AIDS associated Kaposi's sarcoma (Murakamin-Mori, et al. *Int. Immunol.* 8: 595, 1996). The soluble form of the IL-6 receptor (sIL-6Ra) is a potent growth factor for AIDS-associated Kaposi's sarcoma (KS) cells. The soluble form of gp130 is antagonistic for sIL-6Ra-induced AIDS-KS cell growth. Furthermore, high IL-6 levels are associated with weight loss in AIDS.

Proliferative Diseases and Malignancies

An autocrine role for IL-6 has been reported in several types of cancer, among which are renal cell carcinoma, Hodgkin and non-Hodgkin's lymphoma, chronic lymphocytic leukemia, and acute myeloid leukemias. Plasmacytoma and myeloma cells require IL-6 for growth. Treatment of primary plasma cell leukemia with anti-IL-6 antibodies improves the patient's clinical status throughout the treatment. Also, IL-6 deficient mice are completely resistant to plasmacytoma induction.

Multiple myeloma is a malignant proliferation of plasma cells derived from a single clone. It is manifested in a number of organ dysfunctions and symptoms of bone pain or fractures, hypercalcemia, renal failure, susceptibility to infection, anemia and bleeding. The disease typically follows a chronic course for 2 to 5 years before progressing into an acute terminal phase.

The different therapeutic strategies for inhibition of multiple myeloma have been recently reviewed (Ogata A., *Leuk. Res.* 20 : 303, 1996). The vast majority of multiple myeloma patients require systemic chemotherapy to control the malignancy, and symptomatic supportive care to minimize the morbidity. The outcome of patients with multiple myeloma is still unsatisfactory, with median survival times of 2 to 3 years. Clearly, there is a need for an agent that cannot only improve the chances of remission, but also increase the duration of response and enhance survival.

Recently, injection of an anti-IL-6 antibody was tested in young population and resulted in a complete blocking of myeloma cell proliferation and inhibition of the serum IL-6 bioactivity. However, the administration of a single anti-IL-6 mAb appeared to be insufficient (Klein, et al., *Blood* 85: 863, 1995).

IL-6 has also a regulatory role in activation of Matrix Metalloproteinases (MMPs). MMPs are enzymes that are capable degrading the basement membrane components. As such MMPs are refereed as key enzymes in Extra Cellular Matrix remodeling, tumor invasion and metastasis.

Inhibitors of IL-6 Activity

It is generally accepted that IL-6 inhibitors have clinical value. As indicated above there are a number of clinical situations where IL-6 inhibitors could be of therapeutic use. Most of the attempts to produced inhibitors to IL-6 reported in the literature in the past, used proteins. In general, proteins are not very suitable as drugs, due to their immunogenic potential, high cost, and the necessity for parenteral administration. The various attempts to use proteins to inhibit IL-6 are described below.

Monoclonal Antibodies and Antibody Fragments

The most common approach is to use monoclonal antibodies (mAbs). Several murine mAbs capable of inhibiting the bioactivity of IL-6 have been described.

The drawbacks in the use of antibodies against IL-6 are that the mAb traps the IL-6 in an immune complex in the circulation (May et al., *J. Immunol.* 151, 3225, 1993), thereby increasing its half-life 200-fold (Lu et al., *Blood* 86, 3123,1995). The immune complexes are thus serve as long term, slow release deposits of IL-6. The presence of high levels of circulating immune complexes could result in their precipitation in the basal lamina in the kidneys or in the joints, which could lead to kidney failure or arthritis.

Attempts to block IL-6 with monoclonal antibodies have been reported for the following diseases: AIDS associated syndromes and lymphoma (Emilie, et al., *Blood* 84: 2472, 1994), Castelman's disease, rheumatoid arthritis (Wijdenes et al., *J. Interferon Res.* 14: 297, 1994, Yoshizaki et al. *Springer Semin. Immunopathol.*, 20:247, 1998), multiple myeloma, plasma cell leukemia (Klein et al., *Blood* 78: 1198, 1991), and endotoxin toxicity. Partial response were observe in most instances, but the problems associated with the use of monoclonal antibodies for inhibition of IL-6 have so far prevented their routine clinical application.

Some of problems associated with the clinical use of monoclonal antibodies are a result of the large size of the antibody molecule. Minibodies which utilize the hypervariable loop structure of antibodies, capable of inhibiting IL-6 bioactivity were recently reported (Martin et al., *The EMBO J.* 13, 5303, 1994). Binding of IL-6 to a minibody molecule should create a complex that is small enough to be secreted from the kidney, thereby decreasing the risk of creating slow release IL-6 deposits. Minibody-IL-6 complexes may not be recognized as immune complexes, thereby decreasing the chances for kidneys and arthritic problems. The minibodies could still be immunogenic and it is unlikely that they will be orally available. So far, minibodies with sufficiently high affinity for IL-6 have not been obtained.

Mutated Proteins

Several IL-6 mutants were selected for desired activity using phage display systems. Super active mutants were reported (Toniatti, et al., *The EMBO J.* 15: 2726, 1996) as well as mutants which retain the capacity for binding of the IL-6R but lose the ability for interaction with the gp130 and thus could serve as functional antagonists of IL-6 bioactivity (Savino et al., *The EMBO J.* 13,5863, 1994; Sporeno, et al., *Blood* 87: 4510, 1996). The danger in clinical use of such mutants is the formation of antibodies that would recognize both the mutated and the native molecules. Such antibodies could block the bioactivity of IL-6 long after the treatment is terminated thereby exposing the patients to danger associated with lack of IL-6.

U.S. Pat. No. 5,470,952 disclose CTNF and IL-6 antagonists which are heterodimer proteins comprising a soluble α specificity determining cytokine receptor component and the extracellular domain of a β receptor component. Specifically, the inventors claim an IL-6 antagonist, capable of binding IL-6 to form a nonfunctional complex, comprising: soluble IL-6Rα and the extracellular domain of gp130.

Cytokine-toxin Conjugates

Several applications of IL-6 inhibitors entail the elimination of IL-6 dependent tumors, such as multiple myeloma. This goal can be achieved by the use of IL-6-toxin conjugate (Jean and Murphy, *Prot. Eng.* 4, 989, 1991). Malignant cells that have receptor for IL-6 would bind the toxin via the IL-6 portion of the conjugate and would be eliminated by toxin activity. Toxicity to all non-malignant cells that also express the IL-6 receptor is a dangerous possibility. Since IL-6 is required for development of normal humoral and cellular immune response, it is possible to speculate that treated patients would immunocompromised.

Peptide Antagonists of IL-6

Grube and Cochran identified a regulatory domain of the IL-6 receptor (*J. Biol. Chem.* 269: 20791, 1994). The region is from the extramembranal domain of the IL-6R and it is involved in the regulation of IL-6 signal transmission. A synthetic peptide, corresponding to residues 249–264 of the IL-6R inhibits IL-6-dependent cell mitogenesis and IL-6-stimulated acute phase response without affecting ligand binding.

In a search for possible lead compounds, epitope mapping of the human IL-6R was carried out (Halimi et al., *Eur. Cytokin, Netw.* 6:135, 1995) with mabs to IL-6R which inhibit the biological activity of IL-6 (Novick, et al., *Hybridoma* 10, 137, 1991). The 10 mer linear peptides that were recognized by two of the antibodies are from the same region identified by Grube and Cochran (ibid). The peptides identified by these two groups are indicated in the frame of the IL-6R sequence in FIG. 1 (* Grube and Cochran, ** Halimi et al.).

International PCT application WO 97/13781 discloses these synthetic peptides and analogs derived from the IL-6 that inhibit IL-6 activity. The peptides claimed are characterized also by being a linear epitope recognized by one or more Mabs specific to IL-6R. Peptides 1122 and 1123 (Halimi et al. ibid), were synthesized and found to inhibit IL-6 bioactivity in vitro with an $ID_{50}$ of about 100 μM.

International PCT application WO 95/13086 and U.S. Pat. No. 5,420,109, discloses peptides which are cytokine restraining agents having the general formula: X1-X2-His-DPhe-Arg-DTrp-X3. These peptides are non-specific agents which modulate the activity of various cytokines (TNF, IL-1, IL-6 and IL-8) simultaneously, and therefore are not specific IL-6 inhibitors.

International PCT application WO 97/48728, discloses synthetic peptides which derived from IL-6 and from IL-6 receptor (either the IL-6R or gp130), and have IL-6 antagonistic or agonistic activity. The peptides interact with the receptor site of IL-6 or with IL-6Rs present at target cells or when combined, interact with both sites (IL-6 and IL-6R).

U.S. Pat. No. 5,210,075 discloses IL-6 antagonist peptides of varying length, which are modeled after a portion of the sequence of IL-6 itself (p51–70 Hirano et al. *Nature*

324:73, 1986), or which are modeled after four different portions of the sequence of the IL-6 receptor molecule.

None of these disclose conformationally constrained IL-6 peptide antagonists which are cyclized as described in the present invention.

Peptide Mimetic and Backbone Cyclized Peptide Analog Antagonists of IL-6

It is most beneficial to produce conformationally constrained peptide analogs overcoming the drawbacks of the native peptide molecules (low metabolic stability, poor oral bio-availability, rapid liver and kidney excretion, and lack of selectivity), thereby providing improved therapeutic properties.

A novel conceptual approach to the conformational constraint of peptides was introduced by Gilon, et al., (*Biopolymers* 31:745, 1991), who proposed backbone to backbone cyclization of peptides. The theoretical advantages of this strategy include the ability to effect cyclization via the carbons or nitrogens of the peptide backbone without interfering with side chains that may be crucial for interaction with the specific receptor of a given peptide.

Further disclosure by Gilon and coworkers (WO 95/33765) provided methods for producing building units required in the synthesis of backbone cyclized peptide analogs. Recently, The successful use of these methods to produce backbone cyclized peptide analogs having somatostatin activity was also disclosed (WO 98/04583 and WO 99/65508). Libraries of backbone cyclized analogs including IL-6 analogs are disclosed in international application WO 97/09344. In that disclosure, a selection method termed "Cycloscan", based on conformationally constrained backbone cyclic peptide libraries that allows rapid detection of active analogs derived from a given sequence is described.

Nowhere in the background art, are backbone cyclized peptide analogs shown to possess IL-6 inhibitory activity.

SUMMARY OF THE INVENTION

It is an object of the present invention to provide novel peptide analogs, which are characterized in that they incorporate building units with bridging groups attached to the alpha nitrogens of alpha amino acids, having IL-6 inhibitory activity. Specifically, these compounds are backbone cyclized IL-6 antagonists comprising a peptide sequence of five to twenty amino acids that incorporates at least one building unit, said building unit containing one nitrogen atom of the peptide backbone-connected to a bridging group comprising an amide, thioether, thioester or disulfide, wherein the at least one building unit is connected via said bridging group to form a cyclic structure with a moiety selected from the group consisting of a second building unit, the side chain of an amino acid residue of the sequence or the N-terminal amino acid residue. Preferably, the peptide sequence incorporates six to twelve amino acids, having IL-6 inhibitory activity.

Bioactivity of IL-6 requires each of the molecules in the tripartite complex, i.e. IL-6, IL-6R and gp130 signal transducer, to interact with the two other partners. The objectives of the present invention will be achieved by peptides that inhibit any one of interactions in the complex as follows:

a) Peptides derived from IL-6 that interfere with IL-6-IL-6R interaction or with IL-6/gp130 interaction.
b) Peptides derived from IL-6R that interfere with IL-6-IL-6R interaction or with IL-6R/gp130 interaction.
c) Peptides derived from gp130 that interfere with IL-6/gp130 or with IL-6R/gp130 interactions.

According to one aspect of the present invention, the segment of the IL-6R spanning residues 247–271 is currently a most preferred embodiment for development of conformationally constrained backbone cyclized peptide analogs to be used as an inhibitor of IL-6 activity.

From the screening of backbone cyclized peptide analogs, preferred peptide analogs were unexpectedly found to have significantly enhanced inhibitory activity in comparison to the linear epitope. Some of these backbone cyclized peptide analogs mimic the IL-6R inhibitory domain of residues 249–258, others mimic the region in IL-6 which binds its receptor. But unlike the previously described peptides derived from these domains, these novel backbone cyclized peptide analogs possess unique features which make them more suitable for use in pharmaceutical compositions for treatment of pathological conditions associated with elevated levels of IL-6.

According to the present invention it is now disclosed that more preferred backbone cyclized analogs are decapeptide and nonapeptide antagonists of IL-6 with improved activity and metabolic stability. Additional more preferred analogs may advantageously include at least one D-isomer of amino acids in their sequence.

Preferably, the backbone cyclized analogs of the present invention are derived from, or mimic the sequence of the IL-6R molecule, preferably related to residues 247–271 of the IL-6R amino acids sequence. Additional preferred analogs are derived from the sequence of the IL-6 molecule.

A preferred embodiment of the present invention has the following formula:

Formula No. 1

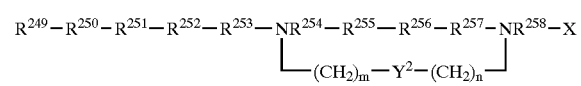

wherein m and n are 1 to 5;

X designates a terminal carboxy acid, amide or alcohol group;

$R^{249}$ is Trp, (L) or (D)Lys, (L) or (D) Tyr or (D)Phe;

$R^{250}$ is Arg;

$R^{251}$ is (L) or (D)Leu or Lys;

$R^{252}$ is (L) or (D)Arg;

$R^{253}$ is (D)- or (L)-Phe;

$R^{254}$ is Ala;

$R^{255}$ is (D)- or (L)-Leu or is Lys;

$R^{256}$ is absent or is (L) or (D) Arg;

$R^{257}$ is (L) or (D) Tyr;

$R^{258}$ is Ala; and $Y^2$ is amide, thioether, thioester or disulfide.

SEQ IDs NO: 1 to NO 32, represent the embodiment of Formula No. 1 when each residue "R" is replaced by its potential amino acid in the L or D configuration. Only one sequence is representing both forms.

A more preferred embodiment of the present invention has the following formula:

Formula No. 2

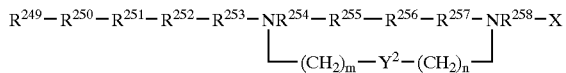

wherein
  m and n are 1 to 5;
  X designates a terminal carboxy acid, amide or alcohol group;
  $R^{249}$ is Trp, (D)Lys or (D)Phe;
  $R^{250}$ is Arg;
  $R^{251}$ is Lys or (D)Leu;
  $R^{252}$ is (D)Arg;
  $R^{253}$ is (D)- or (L)-Phe;
  $R^{254}$ is Ala;
  $R^{255}$ is (D)- or (L)-Leu;
  $R^{256}$ is absent or is Arg;
  $R^{257}$ is (D) Tyr;
  $R^{258}$ is Ala; and
  $Y^2$ is amide, thioether, thioester or disulfide.

Unconventional amino acids which abbreviated in the formulae are as defined hereinbelow.

The currently most preferred backbone cyclized IL-6 antagonists of the invention which are derived from the IL-6 receptor molecule are as follows: Trp-Arg-Lys-(D)Arg-Phe-AlaC3-Leu-Arg-(D)Tyr-AlaN3-NH$_2$ designated herein as PTR-5045 (SEQ ID NO:25); (D)Lys-Arg-(D) Leu-(D) Arg-(D)Phe-AlaC3-(D)Leu-Arg-(D)Tyr-AlaN3-NH$_2$ designated herein as PTR-5041 (SEQ ID NO:18); (D) Phe-Arg-(D)Leu-(D)Arg-(D)Phe-AlaC3-Leu-(D)Tyr-AlaN3-NH$_2$ designated herein as PTR-5043 (SEQ ID NO:4).

These peptide analogs were found to inhibit the cytotoxic effect of IL-6 in various in-vitro bioassays. PTR 5045 was also found to be active in-vivo in prevention of IL-6 induced pathology, and to be metabolically functional bio-stable.

According to another aspect of the present invention, additional preferred analogs are derived from the sequence of the IL-6 molecule. According to the present invention the region of the IL-6 molecule spanning loop AB and helix D, is currently a most preferred embodiment for development of conformationally constrained backbone cyclized peptide analogs to be used as an inhibitor of IL-6 activity.

According to the present invention it is now disclosed that additional more preferred backbone cyclized analogs are hexapeptides antagonists of IL-6 with improved activity and metabolic stability. Additional more preferred analogs may advantageously include at least one D-isomer of amino acids in their sequence.

A preferred embodiment of the present invention, relating to peptides derived from IL-6, has the following formula:

Formula No. 3

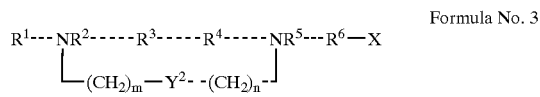

wherein
  m and n are 1 to 5;
  X designates a terminal carboxy acid, amide or alcohol group;
  $R^1$ is (D)Bip, Gln, Lys, Lys(ZCL) or Dab;
  $R^2$ is (D)Lys, Gly, Ala or Trp
  $R^3$ is Orn, 4PyrAla, (L) or (D)Dab, (D)Arg , Lys or Dpr;
  $R^4$ is Lys, Lys(ZCL), Arg, Arg(Mtr) or (D)Glu;
  $R^5$ is Asn, Trp or (D)Ala;
  $R^6$ is Arg, (p-NO2)Phe, (L)- or (D)-Trp, Gln, Abu or Glu; and
  $Y^2$ is amide, thioether, thioester or disulfide.

Another preferred embodiment of the present invention, relating to peptides derived from IL-6, has the following formula:

Formula No. 4

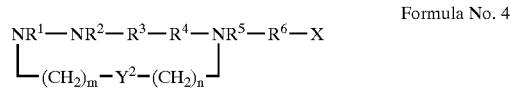

wherein
  m and n are 1 to 5;
  X designates a terminal carboxy acid, amide or alcohol group;
  $R^1$ is (D)Phe or Lys;
  $R^2$ is (D)Cit, Lys or (D)Bip;
  $R^3$ is Dpr, 4PyrAla or (L)- or (D)-Arg;
  $R^4$ is HomArg, Orn or Lys;
  $R^5$ is (D)Gln or (L)- or (D)-Trp;
  $R^6$ is (L)- or (D)-Gln or (p-NO2)Phe; and
  $Y^2$ is amide, thioether, thioester or disulfide.

The currently most preferred backbone cyclized IL-6 antagonists of the invention which are derived from the IL-6 molecule are as follows:

(D)Bip-(D)LysC3-Orn-Lys-AsnN2-Arg-NH$_2$ denoted 70003-20;
(D)Bip-(D)LysC3-4PyrAla-Orn-TrpN2-(p-NO$_2$)Phe-NH$_2$ denoted 70003-41;
(D)Bip-(D)LysC2-Lys-Lys(ZCl)-(D)TrpN2-Abu-NH$_2$ denoted 70003-88;
Gln-GlyC2-(D)Dab-Arg(MTR)-TrpN2-Trp-NH$_2$ denoted 70003-61;
Lys(ZCL)-GlyC2-Dab-(D)Glu-(D)AlaN3-(D)Trp-NH$_2$ denoted 70003-57;
(D)Bip-GlyC2-Dab-(D)Glu-(D)AlaN3-Abu-NH$_2$ denoted 70003-91;
Lys(ZCL)-AlaC2-Dab-(D)Glu-(D)AlaN3-(D)Trp-NH$_2$ denoted 70003-25;
Lys-TrpC2-(D)Arg-Lys-TrpN3-Gln-NH$_2$ denoted 70003-34;
Dab-TrpC2-Dpr-Arg(MTR)-(D)AlaN3-Glu-NH$_2$ denoted 70003-83;
(D)PheC2-(D)Cit-Dpr-HomArg-(D)GlnN2-(D)Gln-NH$_2$ denoted 70003-17;
LysC3-Lys-4PyrAla-Orn-TrpN2-(p-NO2)Phe-NH$_2$ denoted 70003-40; (SEQ. ID. NO;83)
LysC4-Lys-(D)Arg-Lys-TrpN3-Gln-NH$_2$ denoted 70003-33;
(D)PheC2-(D)Bip-Arg-Lys-(D)TrpN2-Gln-NH$_2$ denoted 70003-81.

Preferably, the backbone cyclized peptide analogs of the present invention incorporates two such $N^{\alpha}$-$\omega$-functionalized amino acid derivatives which may be linked to one another to form N-backbone to N-backbone cyclic peptide analogs. Additional preferred analogs of the invention can be constructed with two or more cyclizations, including N-backbone to N-backbone, as well as backbone to side-chain or any other peptide cyclization.

Backbone cyclized analogs of the present invention may be used as pharmaceutical compositions and in methods for the treatment of disorders including: cancers (including multiple myeloma/plasmacytoma), autoimmune diseases (including rheumatoid arthritis, multiple sclerosis, SLE and diabetes), infectious diseases (bacterial and viral infection, septic shock), inflammatory diseases (including pancreatitis), immune deficiency diseases (including AIDS), hematologic diseases (e.g., leukemia, lymphoma), allergic diseases, organ transplantation reactions, Castelman's disease, Lennart's T-cell lymphoma, Non-Hodgkin's lymphoma, Cardiac myxoma, mesangial proliferative glomerulonephritis, polyclonal B-cell activation conditions, abnormal acute phase protein production conditions.

The pharmaceutical compositions comprising pharmacologically active backbone cyclized IL-6 antagonist and a pharmaceutically acceptable carrier or diluent represent another embodiment of the invention, as do the methods for the treatment of a mammal in need thereof with a pharmaceutical composition comprising an effective amount of an IL-6 antagonist according to the invention. Methods of treatment using the compositions of the invention are useful for therapy of cancers (including multiple myeloma/plasmacytoma), autoimmune diseases (including rheumatoid arthritis, multiple sclerosis, SLE and diabetes), infectious diseases (bacterial and viral infection, septic shock), inflammatory diseases (including pancreatitis), immune deficiency diseases (including AIDS), hematologic diseases (e.g., plasma cell dyscrasias, leukemia, lymphoma), allergic diseases, organ transplantation reactions, Castelman's disease, Lennart's T-cell lymphoma, Non-Hodgkin's lymphoma, Cardiac myxoma, mesangial proliferative glomerulonephritis, polyclonal B-cell activation conditions, abnormal acute phase protein production conditions, and osteoporosis using such compositions. The pharmaceutical compositions according to the present invention advantageously comprise at least one backbone cyclized peptide analog which includes at least one D-isomer of amino acids in its sequence. These pharmaceutical compositions may be administered by any suitable route of administration, including topically or systemically. Preferred modes of administration include but are not limited to parenteral routes such as intravenous and intramuscular injections, as well as via nasal or oral ingestion.

DETAILED DESCRIPTION OF THE INVENTION

Definitions

Figure 1:
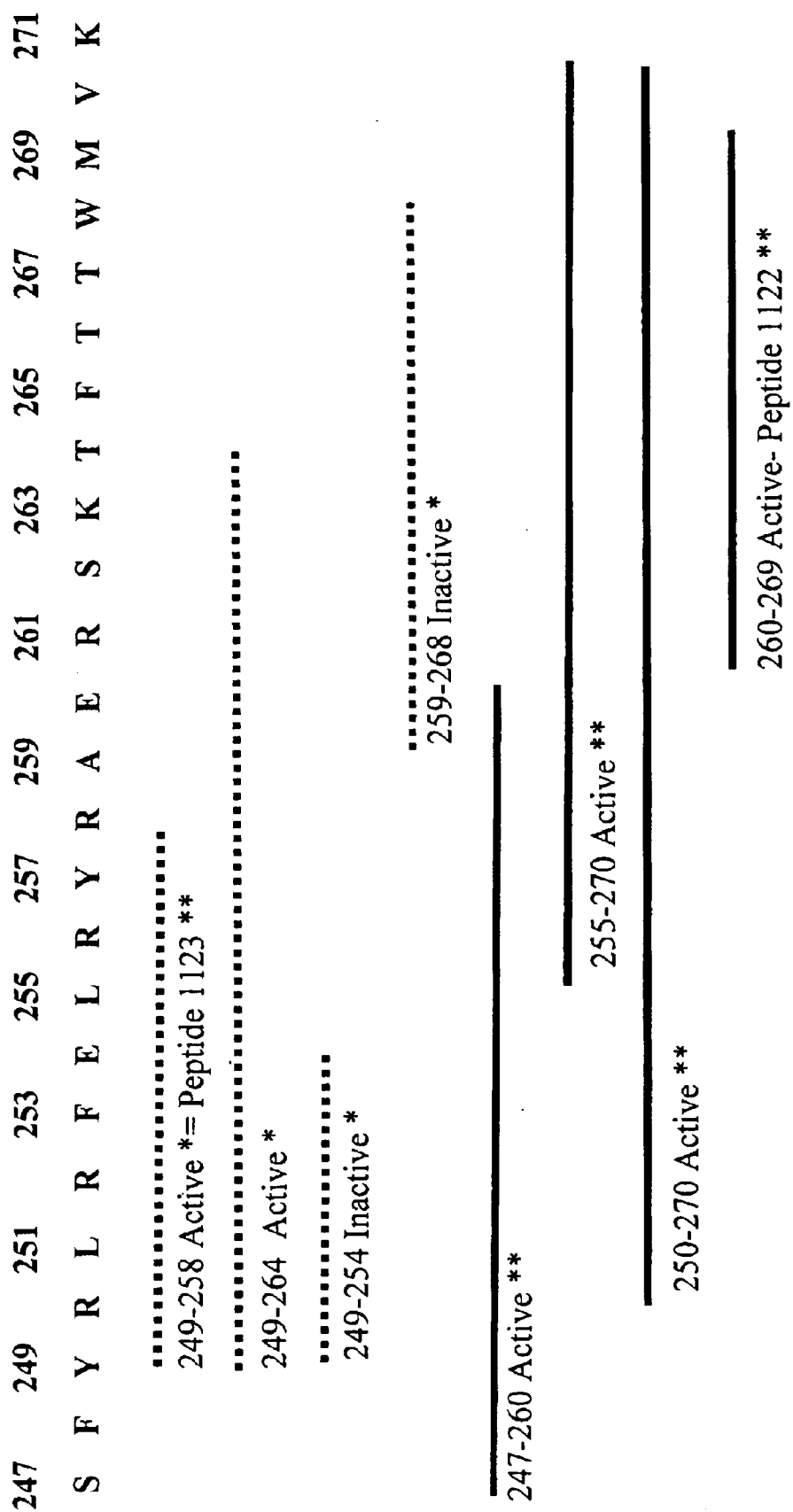
FIG. 1 is a schematic drawing depicting known active IL-6 inhibitory and non-active peptides derived from the IL-6R.

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein and in the claims, the phrase "therapeutically effective amount" means that amount of novel backbone cyclic peptide analog or composition comprising same to administer to a host to achieve the desired results for the indications described herein, such as but not limited of inflammation, cancer, endocrine disorders and gastrointestinal disorders.

The term, "substituted" as used herein, means that any one or more hydrogen atoms on the designated moiety is replaced with a selection from the indicated group, provided that the designated atom's normal valency is not exceeded, and that the substitution results in a stable compound.

When any variable (for example R, X, Z, etc.) occurs more than one time in any constituent or in any Formula herein, its definition on each occurrence is independent of its definition at every other occurrence. Also, combinations of substituents and/or variables are permissible only if such combinations result in stable compounds.

As used herein "peptide" indicates a sequence of amino acids linked by peptide bonds. The IL-6 peptide antagonists of this invention comprise a sequence of amino acids of 4 to 24 amino acid residues, preferably 6 to 16 residues, each residue being characterized by having an amino and a carboxy terminus.

A "building unit" indicates an $N^\alpha$ derivatized a amino acid of the general Formula No. 5:

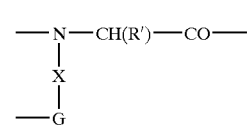

Formula No. 5 wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative.

The methodology for producing the building units is described in U.S. Pat. No. 5,883,293 and International Patent Applications WO 95/33765 and WO 98/04583, both of which are expressly incorporated herein by reference thereto for further details of this methodology. The building units are abbreviated by the three letter code of the corresponding modified amino acid followed by the type of reactive group (N for amine, C for carboxyl), and an indication of the number of spacing methylene groups. For example, GlyC2 describes a modified Gly residue with a carboxyl reactive group and a two carbon methylene spacer, and PheN3 designates a modified phenylalanine group with an amino reactive group and a three carbon methylene spacer.

As used herein "backbone cyclic peptide" or "backbone cyclized peptide" denotes an analog of a linear peptide which contains at least one building unit that has been liked to form a bridge via the alpha nitrogen of the peptide backbone to another building unit, or to another amino acid in the sequence.

As used herein a "PTR" number denotes a reference number assigned to a backbone cyclic peptide analog that is synthesized, purified and fully characterized (e.g., by HPLC, MS, capillary electrophoresis, by amino acid analysis for peptide content and amino acid ratio determination).

As used herein and in the claims, in the formulae of the more preferred backbone cyclic peptide analogs, the superscript numbers following the amino acids refer to their position numbers in the native IL-6 receptor or in the IL-6 molecule.

Abbreviations

Certain abbreviations are used herein to describe this invention and the manner of making and using it. For instance, AcOH refers to acetic acid, Ada refers to adamantanacetyl, Adac refers to adamantanecarbonyl, Alloc refer to allyloxycarbonyl, AIDS refers to acquired immune deficiency syndrome, Boc refers to the t-butyloxycarbonyl radical, BOP refers to benzotriazol-1-yloxy-tris-(dimethylamino)phosphonium hexafluorophosphate, BSA refers to bovine serum albumin, Cbz refers to the carbobenzyloxy radical, CNTF refers to ciliary neurotrophic factor, DCC refers to dicyclohexylcarbodiimide, DCM refers to Dichloromethane, Dde refers to 1-(4,4-dimethy12,6-dioxocyclohex-1-ylidene-ethyl), DIEA refers to diisopropylethyl amine, DMF refers to dimethyl formamide, DPPA refers to diphenylphosphoryl azide, Dtc refers to 5,5-dimethylthiazolidine-4-carboxylic acid, EDT refers to ethanedithiol, ESI-MS refers to electrospray ionization mass spectrometry, Fmoc refers to the fluorenylmethoxycarbonyl radical, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, IL-1 refers to interleukin-1, IL-6 refers to interleukin-6, IL-6R refers to interleukin-6 receptor, IL-11 refers to interleukin-11, KS refers to Kaposi's sarcoma, LC-MS refers to liquid chromatography mass spectrometry, LIF refers to leukocyte inhibitory factor, LIF-R refers to leukocyte inhibitory factor receptor, LPS refers to lipopolysacaride, mAb refers to monoclonal antibody, MMPs refers to Matrix Metalloproteinases, MPS refers to multiple parallel synthesis, MS refers to mass spectrometry, NMM refers to N-methylmorpholine, NMP refers to 1-methyl-2-pyrolidonone, OSM refers to oncostatin M, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, RA refers to Rheumatoid arthritis, RP refers to reverse phase, SLE refers to system lupus ethrythematosus, TBTU refers to 2-(1H-benzotriazole-1-yl)-1,1,3,3-tetramethyluronium tetrafluoroborate, tBu refers to the tertiary butyl radical, TFA refers to trifluoroacetic acid, TIS refers to tri-isopropyl-silane.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, β-Ala refers to β-Alanine, Bip refers to Beta-(4-biphenyl)-alanine, Cit referes to citruline, Dab refers to Diaminobutyric acid, Dpr refers to diaminopropionic acid, HomArg refers to homo arginine, Hcys refer to homocystein, Lys(ZCl) refers to Lys with ε-amino group protected by benzyl chloride, 1Nal refers to 1-naphthylalanine, 2Nal refers to 2-naphtylalanine, Nva refers to norvaline, (p-Cl)Phe refers to para chloro Phenylalanine, (p-NH2)Phe refers to para amino Phenylalanine, (p-F)Phe refers to para fluoro Phenylalanine, (p-NO$_2$)Phe refers to para nitro Phenylalanine, 4PyrAla refers to 4-Pyridylalanine, Thi refers to thienylalanine.

As described earlier, IL-6 plays a pivotal role in mediating immune responses, acute-phase reactions and hematopoiesis. However, it has been shown that the loss of IL-6 regulation, or its overexpression, may be involved in a number of pathological conditions. Specifically, elevated IL-6 levels are detected in bacterial, parasite and viral infections, including HIV, as well as in chronic autoimmune disorders such as rheumatoid arthritis, systemic lupus erythematosus, psoriasis, and multiple sclerosis. In addition, IL-6 is implicated in the pathology of various neoplasms, such as multiple myeloma, leukemia, Kaposi's sarcoma, renal cell carcinoma and cardiac myxoma. In particular, IL-6 has been recognized as the major cytokine required for growth of multiple myeloma tumors and is also possibly involved in the n tumor-associated toxicity in multiple myeloma patients.

It is expected that peptides which inhibit IL-6 function will have broad therapeutic utility in many mammalian diseases. Therapeutic use of backbone cyclized IL-6 peptide antagonists of the present invention is expected to be beneficial in treating a variety of IL-6 associated diseases, many of which are currently treated with immunomodulators or immunosuppresants.

Such IL-6 associated diseases include:
a) Multiple myeloma/plasmacytoma.
b) Autoimmune diseased (including, but not limiting to, rheumatoid arthritis, multiple sclerosis, SLE and diabetes).
c) Infection diseases (bacterial and viral infection, septic shock).
d) Inflammatory diseases.
e) Immune deficiency diseases, including AIDS.
f) Hematologic diseases (e.g., plasma cell dyscrasias, leukemia, lymphoma).
g) Allergic diseases.
h) Organ transplantation reactions.
i) Castelman's disease.
j) Lennart's T-cell lymphoma
k) Non-Hodgkin's lymphoma.
l) Cardiac myxoma.
m) Mesangial proliferative glomerulonephritis.
n) Polyclonal B-cell activation conditions.
o) Abnormal acute phase protein production conditions.
p) Osteoporosis By way of exemplification of the principles of the present invention, a search for inhibitory peptides was focused on the IL-6R/gp130 interface. This was followed by an investigation of the IL-6/IL-6R and the IL-6R/gp130 interfaces. According to one presently preferred embodiment the search comprises mainly rational design and combinatorial libraries screening using multiple parallel synthesis (MPS) approaches.

The advantages of backbone cyclic peptides over existing and previously suggested therapies of multiple myeloma, are as follows:

The suggested IL-6 inhibitor is non-cytotoxic as compared with the currently utilized cytotoxic drugs. The effect of the IL-6 antagonist would be specific to multiple myeloma cells and a small subset of IL-6 dependent cells, where the other cytotoxic drugs are non-selective and kill all types of dividing cells in the body.

The suggested IL-6 antagonist is small and thus non-immunogenic by nature, as compared to the potentially immunogenic antibodies, antibody fragments and minibodies.

The suggested IL-6 antagonist could be modified to be orally bioavailable. It is unlikely that proteins (antibodies, fragments or minibodies) would be orally available.

Over 7400 individual backbone cyclized peptide analogs were synthesized in MPS format and tested by at least one type of bioassay for inhibition of IL-6 bioactivity.

The best peptides achieved at this screening stage, demonstrated an estimated $IC_{50}$ around 1 μM. This represents 10 to 100 fold improvement of peptide analogs available as linear peptides derived from the IL-6R molecule.

About 50 peptide analogs (PTRs), chosen by activity from the MPS syntheses, were synthesized in large scale, purified and fully characterized. These PTRs were tested for IL-6 inhibitory activity in at least one in-vitro bioassay.

From the above described massive screening of backbone cyclized peptide analogs in MPS and PTR format three peptides were unexpectedly found as particularly active. These backbone cyclized peptide analogs mimic the IL-6R inhibitory domain of residues 249–258, and the region in IL-6 which binds to the receptor. But unlike the previously described peptides derived from these domains, these novel backbone cyclized peptide analogs possess unique features which make them more suitable for use in pharmaceutical compositions for treatment of pathological conditions associated with elevated levels of IL-6.

The preferred backbone cyclized IL-6 antagonists of the present invention are now described.

One embodiment has the following formula:

Formula No. 1

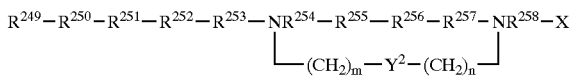

wherein m and n are 1 to 5;

X designates a terminal carboxy acid, amide or alcohol group;

$R^{249}$ is Trp, (L) or (D)Lys, (L) or (D) Tyr or (D)Phe;

$R^{250}$ is Arg;

$R^{251}$ is (L) or (D)Leu or Lys;

R252 is (L) or (D)Arg;

$R^{253}$ is (D)- or (L)-Phe;

R254 is Ala;

$R^{255}$ is (D)- or (L)-Leu or is Lys;

$R^{256}$ is absent or is (L) or (D) Arg;

$R^{257}$ is (L) or (D) Tyr;

$R^{258}$ is Ala; and $Y^2$ is amide, thioether, thioester or disulfide.

A currently more preferred embodiment has the following formula:

Formula No. 2

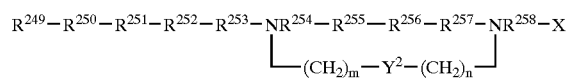

wherein m and n are 1 to 5;

X designates a terminal carboxy acid, amide or alcohol group;

$R^{249}$ is Trp, (D)Lys or (D)Phe;

$R^{250}$ is Arg;

$R^{251}$ is Lys or (D)Leu;

$R^{252}$ is (D)Arg;

$R^{253}$ is (D)- or (L)-Phe;

$R^{254}$ is Ala;

$R^{255}$ is (D)- or (L)-Leu;

$R^{256}$ is absent or is Arg;

$R^{257}$ is (D) Tyr;

$R^{258}$ is Ala; and $Y^2$ is amide, thioether, thioester or disulfide.

A most preferred compound according to this embodiment is denoted PTR 5045 wherein the residues are as follows:

$R^{249}$ is Trp;

$R^{250}$ is Arg;

$R^{251}$ is Lys;

$R^{252}$ is (D)Arg;

$R^{253}$ is Phe;

$R^{254}$ is Ala;

$R^{255}$ is Leu;

$R^{256}$ is Arg;

$R^{257}$ is (D)Tyr;

$R^{258}$ is Ala; and $Y^2$ is amide.

Another preferred compound according to this embodiment is denoted PTR 5041 wherein the residues are as follows:

$R^{249}$ is (D)Lys;

$R^{250}$ is Arg;

$R^{251}$ is (D)Leu;

$R^{252}$ is (D)Arg;

$R^{253}$ is (D)Phe;

$R_{254}$ is Ala;

$R^{255}$ is Leu;

$R^{256}$ is Arg;

$R^{257}$ is (D) Tyr;

$R^{258}$ is Ala; and $Y^2$ is amide.

Another preferred compound according to this embodiment is denoted PTR 5043 wherein the residues are as follows:

$R^{249}$ is (D)Phe;

$R^{250}$ is Arg;

$R^{251}$ is (D)Leu;

$R^{252}$ is (D)Arg;

$R^{253}$ is (D)Phe;

$R^{254}$ is Ala;

$R^{255}$ is Leu;

$R^{256}$ is absent;
$R^{257}$ is (D)Tyr;
$R^{258}$ is Ala; and
$Y^2$ is amide.

Another preferred embodiment of the present invention, relating to peptides derived from IL-6, has the following formula:

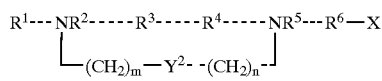

Formula No. 3 wherein m and n are 1 to 5;

X designates a terminal carboxy acid, amide or alcohol group;

$R^1$ is (D)Bip, Gln, Lys, Lys(ZCL) or Dab;

$R^2$ is (D)Lys, Gly, Ala or Trp $R^3$ is Orn, 4PyrAla, (L) or (D)Dab, (D)Arg, Lys or Dpr;

$R^4$ is Lys, Lys(ZCL), Arg, Arg(Mtr) or (D)Glu;

$R^5$ is Asn, Trp or (D)Ala;

$R^6$ is Arg, (p-NO2)Phe, (L)- or (D)-Trp, Gln, Abu or Glu; and $Y^2$ is amide, thioether, thioester or disulfide.

Another preferred embodiment of the present invention, relating to peptides derived from IL-6, has the following formula:

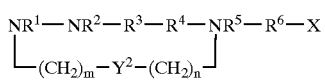

Formula No. 4 wherein m and n are 1 to 5;

X designates a terminal carboxy acid, amide or alcohol group;

$R^1$ is (D)Phe or Lys;

$R^2$ is (D)Cit, Lys or (D)Bip;

$R^3$ is Dpr, 4PyrAla or (L)- or (D)-Arg;

$R^4$ is HomArg, Orn or Lys;

$R^5$ is (D)Gln or (L)- or (D)-Trp;

$R^6$ is (L)- or (D)-Gln or (p-NO2)Phe; and $Y^2$ is amide, thioether, thioester or disulfide.

The most preferred backbone cyclized IL-6 antagonists of the invention described in table 1:

TABLE 1

The most preferred analogs of the invention.

| | |
|---|---|
| PTR 5045 | Trp-Arg-Lys-(D)Arg-Phe-AlaC3-Leu-Arg-(D)Tyr-AlaN3-X |
| PTR 5041 | (D)Lys-Arg-(D)Leu-(D)Arg-(D)Phe-AlaC3-(D)Leu-Arg-(D)Tyr-AlaN3-X |
| PTR 5043 | (D)Phe-Arg-(D)Leu-(D)Arg-(D)Phe-AlaC3-Leu-(D)Tyr-AlaN3-X |
| 70003-20 | (D)Bip-(D)LysC3-Orn-Lys-AsnN2-Arg-X |
| 70003-41 | (D)Bip-(D)LysC3-4PyrAla-Orn-TrpN2-(p-NO$_2$)Phe-X |
| 70003-88 | (D)Bip-(D)LysC2-Lys-Lys(ZCl)-(D)TrpN2-Abu-NH$_2$ |
| 70003-61 | Gln-GlyC2-(D)Dab-Arg(MTR)-TrpN2-Trp-X |
| 70003-57 | Lys(ZCL)-GlyC2-Dab-(D)Glu-(D)AlaN3-(D)Trp-NH$_2$ |
| 70003-91 | (D)Bip-GlyC2-Dab-(D)Glu-(D)AlaN3-Abu-NH$_2$ |
| 70003-25 | Lys(ZCL)-AlaC2-Dab-(D)Glu-(D)AlaN3-DTrp-X |
| 70003-34 | Lys-TrpC2-(D)Arg-Lys-TrpN3-Gln-X |

TABLE 1-continued

The most preferred analogs of the invention.

| | |
|---|---|
| 70003-83 | Dab-TrpC2-Dpr-Arg(MTR)-(D)AlaN3-Glu-X |
| 70003-17 | (D)PheC2-(D)Cit-Dpr-HomArg-(D)GlnN2-(D)Gln-X |
| 70003-40 | LysC3-Lys-4PyrAla-Orn-TrpN2-(p-NO2)Phe-X |
| 70003-33 | LysC4-Lys-(D)Arg-Lys-TrpN3-Gln-NH$_2$ |
| 70003-81 | (D)PheC2-(D)Bip-Arg-Lys-(D)TrpN2-Gln-X | where X is -NH$_2$ or -OH and the bridging group extends between the two building units.

A more preferred embodiment of the invention incorporates two $N^\alpha$-ω-functionalized amino acid derivatives which may be linked to one another to form N-backbone to N-backbone cyclic peptide analogs.

The most striking advantages of backbone cyclization are:

1) Cyclization of the peptide sequence is achieved without compromising any of the side chains of the peptide thereby decreasing the chances of sacrificing functional groups essential for biological recognition and function.

2) Optimization of the peptide conformation is achieved by allowing permutation of the bridge length, direction, and bond type (e.g., amide, disulfide, thioether, thioester, etc.) and position of the bond in the ring.

3) When applied to cyclization of linear peptides of known activity, the bridge can be designed in such a way as to minimize interaction with the active region of the peptide and its cognate receptor. This decreases the chances of the cyclization arm interfering with recognition and function, and also creates a site suitable for attachment of tags such as radioactive tracers, cytotoxic drugs, light capturing substances, or any other desired label.

Peptide analogs can be constructed with two or more cyclizations, including N-backbone to N-backbone, as well as backbone to side-chain or any other peptide cyclization. The second cyclization, can be formed by incorporating at least one additional building unit into a peptide sequence and linking it to another building unit, to the amino acid side chain or to any of the peptide terminals. In addition the second cyclization can be a side-chain to side-chain (including di-sulfide bond), or a side-chain to terminal cyclization.

It has now unexpectedly been found that the backbone cyclized IL-6 antagonists of the present invention which were identified by screening of individual backbone cyclized peptide analogs that were synthesized and assayed for inhibition of IL-6 activity, are 10–100 folds more active than the linear IL-6 inhibitory peptides previously described.

The backbone cyclic peptides of this invention are novel analogs which mimic the IL-6R inhibitory domain of residues 249–258. The amino acid sequence of the backbone cyclic analogs is based on what was identified as the most active inhibitory fragment of the IL-6R (Grube and Cochran, ibid). Additional analogs mimic a non-continuos region of the IL-6 molecule, comprising the contact residue of IL-6 to its receptor. These analogs have an additional advantage of having molecular weights of around 1000 dalton.

The present innovative backbone cyclic analogs preferably include 5 to 20 amino acids with special amino acid modifications. Specifically, at least one amino acid in each analog is a D-isomer of the amino acid.

The special feature of the novel backbone cyclic peptide analogs is their metabolic stability as tested in vitro against degradation of the most aggressive enzyme mixture in the body (e.g., renal homogenate). PTR 5045 is stable under these conditions for up to 24 hours. The previously described peptide analogs derived from the IL-6R, and fragments of the native protein, are significantly less stable metabolically.

General Method for Synthesis, Purification and Characterization of Backbone Cyclic Peptides Synthesis Resin: 1 g Rink amide or Tenta-gel resin, with loading of 0.2–0.7 mmol/gr.

Fmoc-deprotection performed with 7 mL of 20% piperidine in NMP. Twice for 15 minutes following 5 washes with 10 ml NMP for 2 minutes with shaking.

Couplings

1. Regular couplings (coupling to simple amino acids): with a solution containing 3 equivalents amino acid, 3 equivalents PyBroP and 6 equivalents of DIEA in 7 ml NMP. For 0.5–2 hours with shaking. Coupling is monitored by ninhydrine test and repeated until the ninhydrine solution become yellow.
2. Coupling of His and Asn with a solution containing 5 equivalents DIC and 5 equivalents HOBT in 10 ml DMF.
3. Coupling to Gly building units: with a solution containing 3 equivalents amino acid, 3 equivalents PyBroP and 6 equivalents DIEA in 7 ml NMP. Twice for 1–4 hours with shaking.
4. Coupling to building units which are not Gly: with a solution containing 5 equivalents amino acid, 1.5 equivalents triphosgene and 13 equivalents collidine in 15 ml dioxane or THF. Twice for 0.5–2 hours at 50° C. with shaking.

Removal of the Allyl and Alloc protecting groups of the building units performed with 1.5 equivalents per peptide of $Pd(PPh_3)_4$ in 30 ml DCM containing 5% acetic acid and 2.5% NMM. For 1–4 hours with shaking.

Cyclization performed with a solution containing 3 equivalents PyBOP and 6 equivalents DIEA in 7 ml NMP. For 0.5–2 hours with shaking. Cyclization is monitored by ninhydrine test and repeated if necessary.

Cleavage performed using 82%–95% TFA supplemented with scavengers: 1–15% $H_2O$, 1–5% TIS and 1–5% EDT.

Purification

An individual purification method for each backbone cyclic peptide is developed on analytical HPLC to give the maximum isolation of the cyclic peptide from other crude components. The analytical method is usually performed using a C-18 Vydac column 250X4.6 mm as the stationary phase and water/ACN containing 0.1% TFA mixture gradient.

The preparative method is designed by implying the analytical separation method on the 2" C-18 Vydac preparative method. During the purification process, the peak containing the cyclic peptide is collected using a semi-automated fraction collector. The collected fractions are injected to the analytical HPLC for purity check. The pure fractions are combined and lyophilized.

Characterization

The combined pure lyophilized material is analyzed for purity by HPLC, MS and capillary electrophoresis and by amino acid analysis for peptide content and amino acid ratio determination.

General Method for Synthesis, Purification and Characterization and Screening of Backbone Cyclic Peptides in MPS Format The MPS procedure is used as the routine peptide development procedure. Individual peptides, or groups of a few peptides, are synthesized in 96-wells microtiter plates equipped with filters that allow passage of solvent but not of solid phase matrix. A simple and efficient valve apparatus that enables simultaneous closing and opening of all the valves (produced by Millipore) is used. The system utilizes an Approach in which each well is equipped with a solvent permeable membrane at the bottom that does not allow passage of particles above a certain size. The process allows one to place resin in the wells, perform reaction in solvent, and remove the solvent from all the wells simultaneously by applying vacuum. These special plates, which are available in the standard 96 well format allow the parallel synthesis of 96 peptides simultaneously. The synthesis scale of the procedure is in the range of 1–5 $\mu$mole per well. Following purification by C18 reverse phase columns (SepPak purification), which is also carried in the standard 96 well format, the peptides are routinely dissolved in 1 ml of water to yield a theoretical crude concentration of 1–5 mM (depending on synthesis scale). Monitoring of chemical quality of the resulting peptides is performed by ESI-MS analysis. Analysis of several plates prepared on different occasions by different operators indicated a general success rate of about 80% as judged by the presence of the desired peptide mass in the crude preparation. Further analysis of a peptides from MPS is carried out by LC-MS. The analysis revealed crude peptide quality similar to crude preparations of peptides synthesized individually in large scale. Different steps or the complete process are now performed automatically using automatic peptide synthesizers. Peptides are tested for bioactivity at a dilution of 1:40 (theoretical crude concentration of 125 $\mu$M), or higher, which apparently eliminated most of the toxic effects and enabled routine biological testing of peptides.

Detailed Procedure for Synthesis in MPS Format

For capacity of 5 $\mu$mole 10 mg resin with a substitution of 0.5 mmol/gr is used.

Fmoc Deprotection

To each well 100 $\mu$l of 20% piperidine in NMP are added. The reaction shacked for 15 min. The NMP is removed by suction.

Washing after Fmoc deprotection: the resin is washed by placing 150 $\mu$l NMP into each well followed by evacuation of the solution by vacuum. This process is repeated 4 times.

Coupling using PyBroP

Well capacity: 5 $\mu$mol
Amount of amino acid per coupling per well: 26 $\mu$mol
Amino acid in NMP concentration: 650 mM
Amino acid volume used: 40 $\mu$l
PyBroP amount: 26 $\mu$mol
PyBroP concentration: 403 mg/ml
PyBroP volume used: 30 $\mu$l
DIEA added: 10 $\mu$l
Total reaction volume: 80 $\mu$l The amino acids are added to the pre-activation plate, then a fresh solution of PyBroP is distributed into this plate followed by addition of DIEA. The solution from this plate is transferred to the reaction plate and shacked for 1 hour. This coupling is repeated twice.

Coupling Using Mukayama Reagent

Amino acid solution at 650 mM—40 $\mu$l
Mukayama reagent at 111 mg/ml—60 $\mu$l
Collidine added per well—15 $\mu$l The same procedure as for coupling with PyBroP. Reaction temperature 50° C., reaction time: first coupling 4h, second coupling 16h.

Allyl Alloc deprotection: this step is performed after completing the assembly, by addition of 180 $\mu$l solution of 1.5 g $Pd(PPh_3)_4$ in 20 ml $CH_2Cl_2$ containing 5% AcOH+ 2.5% NMM.

Cyclization—this step is performed by addition of 100 μl solution of PyBoP in NMP+DIEA.

Cleavage of the Peptide from the Resin and SepPak Purification

After final Fmoc deprotection the resin is transferred into a deep well microtiter plate, to each well 300 μl of TFA solution containing 2.5% TIS, 2.5% H₂O, 2.5% EDT are added. Removal of the TFA is performede by lyophilization. After cleavage the peptides are purified by SepPak.

Screening of IL-6 Antagonists for Biological Activity

In-vitro Bioassays

Screening for bioactivity of potential IL-6 inhibitory peptides was performed in vitro. Inhibition of IL-6 results in the death of IL-6 dependent cell lines such as the murine T1165 and B9, or the human TF1 and XG1. Alternatively, inhibition of IL-6 can be monitored by following the IL-6 induced differentiation of A375, B16.F10.9 and M1 cells which results in continued growth of the cells. Measuring IgG secretion by CESS cell line can also be used for monitoring IL-6 inhibitory activity.

Five types of in vitro bioassays for IL-6 inhibition using different murine and human cell lines were used in different stages of the search, for screening of inhibitory peptides.

Bioassay Using B9 Cells

B9 (murine myeloma) cells require IL-6 for growth. Inhibition of IL-6 results in cell death. The assay procedure was performed as described in Halimi et al. (ibid).

Bioassay Using T1165 Cells

T1165 (murine myeloma cells) require IL-6 for growth and die if IL-6 is omitted or inhibited. The validity of the assay was demonstrated by inhibition of IL-6 bioactivity using rabbit IL-6 antiserum.

Bioassay Using B16.F10.9 Melanoma Cells

The F10.9 sub-line of B16 (murine melanoma) expresses gp130 but not IL-6R. Addition of human IL-6 and human IL-6R, or a chimera of IL-6/IL-6R results in differentiation which is associated with growth arrest of the cells. Inhibition of IL-6 results in continued growth. Since the end point of this assay is cell growth rather than cell death, this assay system was used primarily in order to differentiate between suspected toxic effects observed on B9 or T1165 cells, and true inhibition of IL-6 activity.

The B16.F10.9 cell assay was routinely used as a confirmation assay for the T1165 or TF1 assay which were the primary screening assays (at different stages of the search).

Evaluation of the results in this assay is possible using two methods. One method uses vital dyes for monitoring cell growth. The second method comprises visual observation of the cell morphology and establishing a cut off point based on the following observations:

Cells which are not treated with IL-6 create a monolayer that covers almost all the surface area. Treatment with IL-6 causes growth arrest and a morphological change: the cells become very narrow and elongated as compared to the more spread out shape of the non-treated cells. Treatment of the cells with IL-6 and an inhibitory peptide apparently completely restores cell growth but does not completely restores the cell morphology. Treatment of cells with IL-6 and a non-inhibitory peptide results in cells that appear to be very similar to the IL-6 treated cells.

Based on such observations, the results of the assay are reported as the last concentration of the peptide that cause almost complete inhibition of the effect of IL-6.

Bioassay Using A375 Cells

The A375 are human melanoma cells. IL-6 induces differentiation of A375 cells which is associated with growth arrest similar to the phenomenon observed with the B16F10.9 murine melanoma cells. Thus, inhibition of IL-6 results in continued growth of the cells which is easily quantifiable. In such case toxicity of peptides would register as a false negative rather than false positive. This conditions is preferable during screening process. Second, since these are human cells, the molecules involved in the bio-response, i.e. IL-6, IL-6R and gp130 are all of human origin thus ensuring authenticity of the tested peptide bioactivity. Another advantage of the A375 cells is their ability to be induced by other cytokines that share the gp130 signal transducer, i.e. leukemia inhibitory factor (LIF) and oncostatine M (OSM). As can be seen in table 2, LIF alone does not affect A375 cells, unless the respective receptor (LIF-R) is also added. Apparently the A375 line we use lacks LIF-R. OSM is highly effective alone. The availability of this assay system, allows us to test, the specificity of our IL-6 inhibitory peptides vs. other cytokines of the family, in an array of assays all using a single cell line. Assay performance is described in Savino et al. (ibid).

TABLE 2

Inhibition of A375 by cytokines other than IL-6

| Cytokine | Concentration (ng/ml) | % Inhibition (relative to IL-6)* |
| --- | --- | --- |
| LIF | 1 | 1 |
| LIF | 10 | 2 |
| LIF + LIFR | 10 | 45 |
| OSM | 1 | 94 |
| OSM | 10 | 141 |

*The maximal (plateau) inhibitory activity of IL-6 on A375 cells was taken as 100%

The assay was validated using rabbit IL-6 antiserum which was used to inhibit the bioactivity of IL-6. Testing of crude peptide preparations, as well as high concentrations of purified peptides resulted in marked toxicity to the cells. Further results indicated that the toxicity is dose dependent and decreases with increasing dilution of the crude peptide preparation, or at low concentration of the purified peptides. It is therefore anticipated that the assay can be used for screening of analogs with nM activity. It can be also used for specifically screening for demonstration of peptide selectivity in the context of gp130 related cytokines in order to differentiate between peptides that inhibit IL-6 alone and peptides that inhibit IL-6 and additional, gp130 using cytokines.

Bioassay Using TF1 Cells

TF1 cells (human erythroleukemia) cells require IL-6 for growth and thus inhibition of IL-6 bioactivity results in cell death, similar to T1165 cells. The origin of all relevant molecules is human.

The problem associated with toxicity (false positive results), could be overcome in the TF1 based assay since these cells can be induced by additional cytokines which are unrelated to IL-6 (not using the gp130 signal transducer). It, is possible to induce the cells to grow with IL-6 and with additional cytokine e.g. GM-CSF. Specific inhibition of IL-6 bioactivity is therefore expected to register only in cells induced by IL-6 and not with GM-CSF. Validity of the use of TF1 cells and of the differential inhibition concept was demonstrated by the use of rabbit IL-6 antiserum. Only the IL-6 induced growth was inhibited by the antiserum. Assay procedure is based on the procedure described in Fourcin et al. (ibid). The amount of viable cells at the end of the assay is determined by staining the cells with WST reagent as well as by measuring thymidine corporation ($^3$H-T).

Inhibition of the IL-6 using peptides derived from the IL-6R or from gp130, but not from the IL-6 itself could result in inhibition of other cytokines that also utilize the gp130 signal transduction system. In order to test the specificity of the peptide analogs in that respect, bioassays for the bioactivity of some of the other cytokines in the groups (i.e. IL-11, CNTF, OSM), are performed.

In-vitro Binding Assays

Binding assays are intended to measure the direct effect of the peptide on formation of the IL-6 active hexamer. Unlike the bioassays, the use of this assay could clearly demonstrate the mode of activity of the tested peptides. A simple format for such assay would be as follows: IL-6, IL-6R and soluble gp130 would be mixed in solution together with the test peptide. Capture of the putative hexamer would be achieved by an anti-gp130 antibody and detection of the bound complex would be achieved by antibody to either IL-6 or IL-6R. A separate assay performed in order to test the interference of the peptide in the IL-6/IL-6R interaction.

Assays of similar format are used for testing the inhibition specificity of the peptide to the IL-6 bioactive complex by replacing the IL-6-IL-6R complex with commercially available cytokines and receptors of the other cytokines known to utilize the gp130 signal transducer.

In-vivo Assays

The prime clinical target for the IL-6 antagonist is multiple myeloma. In-vivo model systems are performed in mice inoculated with murine IL-6 dependent myeloma cell lines. Nude mice grafted with human multiple myeloma cells are also used. Other in-vivo assays which are used for testing the inhibitory effects of the backbone cyclized IL-6 antagonists are: IL-6 mediated acute-phase response, IL-6 mediated adjuvant arthritis, and pancreatitis induced by taurocholic acid as described in the following examples.

The skilled artisan will appreciate that the following examples are merely illustrative and serve as non limitative exemplification of the principles of the present invention and that many variations and modifications are possible within the scope of the currently claimed invention as defined by the claims which follow.

EXAMPLES

Example 1

Detailed Synthesis of PTR 5045 (SEQ ID NO:25) Trp-Arg-Lys-(D)Arg-Phe-AlaC3-Leu-Arg-(D)Tyr-AlaN3-NH$_2$ Two grams of Tenta-Gel resin (0.22 mmol/g), were swelled in NMP in a reaction vessel equipped with a sintered glass bottom and placed on a shaker. All the Fmoc protecting groups were removed by reaction with 20% piperidine in NMP (2 times 10 minutes, 10 ml each) followed by NMP wash (5 times two minutes, 15 ml each). Fmoc removal was monitored by ultraviolet absorption measurement at 290 nm. The couplings of the amino acids: Fmoc-Arg(pmc)-OH, Fmoc-Leu-OH, Fmoc-(D)Arg(pmc)-OH, Fmoc-Lys(Boc)-OH, Fmoc-Arg(pmc)-OH, Fmoc-Trp(Boc)-OH were carried out with 4 eq (1.76 mmol) of the amino acid+PyBrop (4 equivalents, 1.76 mmol)+DIEA (8 equivalents, 3.52 mmol) in NMP (10 ml) for 1.5 hour at room temperature. Reaction completion was monitored by the qualitative ninhydrin test (Kaiser test). After each coupling, the peptide-resin was washed with NMP (5 times with 15 ml NMP, 2 minutes each). The coupling of Fmoc-(D)Tyr(t-Bu)-OH to AlaN3 building unit was carried out by use of 4 eq of amino acid+a mixture of TPTU and ToPPyU(4 eq, 1.76 mmol) in 10 ml NMP+8 eq DIEA, double coupling: first coupling 2h, second coupling overnight. The coupling of Fmoc-Phe-OH to AlaC3 building unit was carried out by the same manner. Coupling completion was monitored by HPLC . The Allyl/Aloc protecting groups were removed by reaction with Pd(PPh$_3$)$_4$ and acetic acid 5%, morpholine 2.5% in CH$_2$Cl$_2$, under argon, for 2 hours at room temperature. The peptide resin was washed with CHCl$_3$(3 times, 5 min 30 ML each) followed by NMP. Cyclization was carried out with PyBOP 3 equivalents, DIEA 6 equivalents, in NMP, at room temperature for 2h. Final Fmoc deprotection was carried out with 20% piperidine in NMP as above. The peptide resin was washed with CH$_2$Cl$_2$ and dried under reduced pressure. The peptide was cleaved from the resin by reaction with TFA 94%, water 2.5%, EDT 2.5%, TIS 1%, at 0° C. for 15 minutes and 2 hours at room temperature under argon. The mixture was filtered and the resin was washed with a small volume of TFA. The filtrate was placed in a rotary evaporator and all the volatile components were removed. An oily product was obtained. It was triturated with ether and the ether decanted, three times. A white powder was obtained. This crude product was dried. The weight of the crude product was 400 mg. After purification by HPLC a single peak was obtained with 100% purity as detected by analytical HPLC and capillary electrophoresis. The expected mass of 1489.7 daltons was detected by mass spectroscopy.

Example 2

Figure 2:
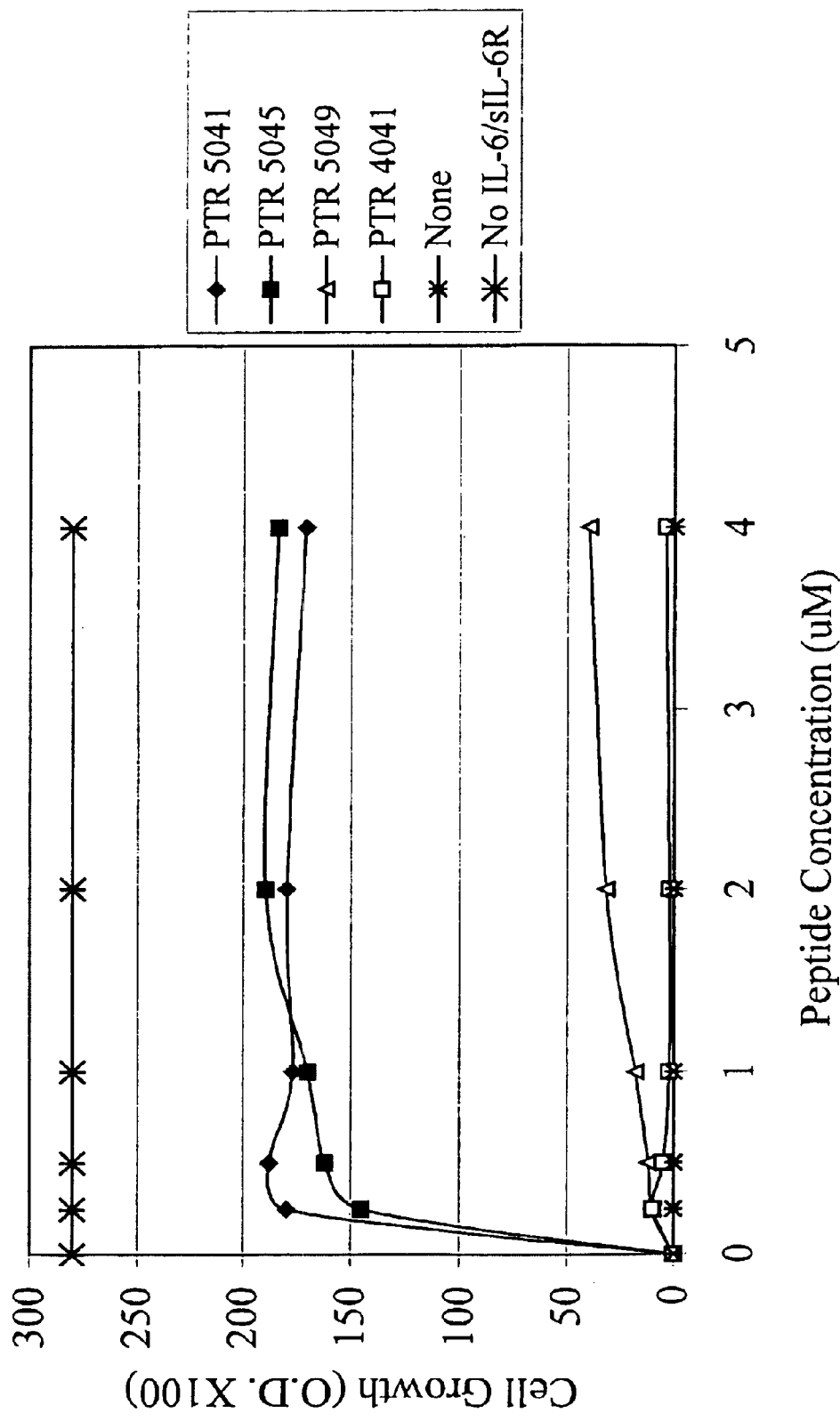
FIG. 2 describes the effect of backbone cyclic peptide analogs on B16.F10.9 melanoma cells growth.

The Effect of Backbone Cyclic Peptide Analogs on B16.F10.9 Melanoma Cells Growth Peptides were added to B16.F10.9 melanoma cells in the presence of 200 ng/ml IL-6 and 125 ng/ml sIL-6R. Incubation for three days. (Peptide concentration was calculated for average molecular weight of 1500 Da. Sequence of control peptides; PTR 5049 (L Form of SEQ ID NO:25): Trp-Arg-Lys-(D)Arg-Phe-AlaC3-Leu-Arg-Tyr-AlaN3-NH$_2$. The results described in FIG. 2 show that PTR 5045 (SEQ ID NO:025) and PRT 5041 (SEQ ID NO:18) fully block IL-6 activity at concentration of about 250 nM while PTR 5049 (L Form of SEQ ID NO:25) and PTR 4041 (SEQ ID NO:33) are not active.

Example 3

The in-vivo Effect of IL-6 Antagonists on IL-6 Mediated Acute-phase Response

The objective was to establish a simple first-line in-vivo model, for testing the activity of IL-6 inhibitors. The turpentine model was chosen based on the principal role that IL-6 plays in this inflammatory response.

Systemic and localized inflammation elicit a general reaction in the organism, known as the acute phase response, which includes fever, loss of body weight, hypoglycemia, and changes in the serum levels of several plasma proteins produced by the liver. IL-6 is an important mediator of the acute-phase reaction (see Heinrich et.al., *Biochemistry J.* 1 265:621, 1990 for a comprehensive review), together with IL-1 and TNF-α. It has been shown previously that sterile tissue damage caused by injection of turpentine induces an acute-phase reaction, and that IL-6 is an essential mediator of this response (Rokita et.al., *Cytokine* 5:454, 1993).

To confirm this role of IL-6 in this phenomenon we used IL-6-deficient mice generated by gene targeting (knock out). Method and Results IL-6 knock-out (-/-) and matched wild-type (C57/Black; CB) mice were used. Sterile tissue damage was induced by subcutaneous injection of turpentine, 0.1 ml, into both hind limbs. IL-6 was determined in the serum by ELISA (QuantikineM, R&D). For liver acute-phase proteins, Fibrinogen was determined in citrated plasma, by the calcium method.

Figure 3A:
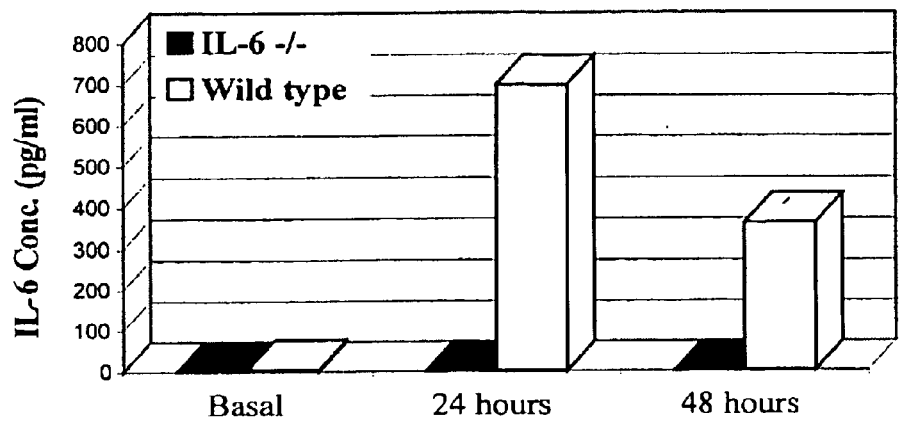
FIG. 3 describes in-vivo effects of IL-6 antagonists on IL-6 mediated acute-phase responses: a) IL-6 serum levels, b) fibrinogen plasma levels and c) changes in body weight, in normal and IL-6 knockout mice.
Figure 3B:
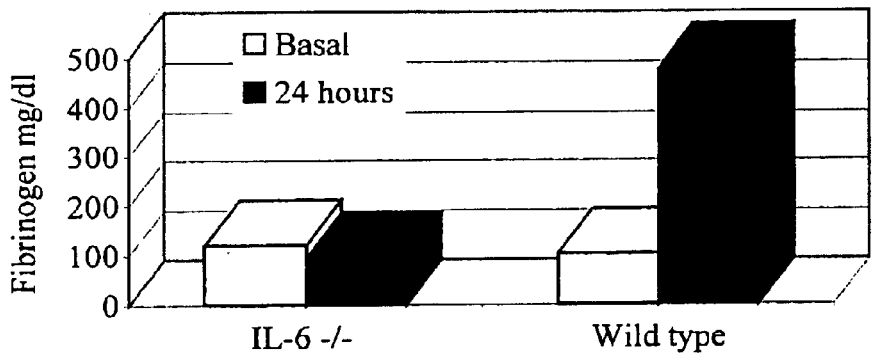

IL-6 levels rose 7-fold following turpentine injection in normal, but not in IL-6 deficient mice (FIG. 3a). Fibrinogen levels rose 3- to 4-fold following turpentine injection in normal, but not in IL-6 deficient mice (FIG. 3b).

Figure 3C:
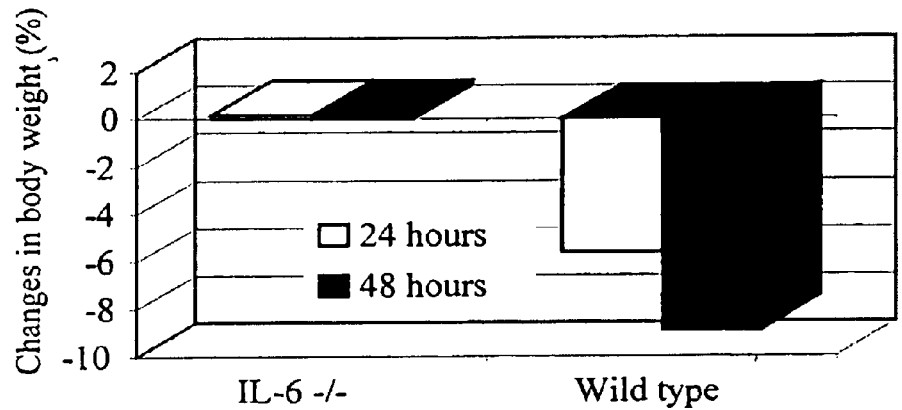

Loss of body weight occurred following turpentine injection in normal, but not in IL-6 deficient mice (FIG. 3c).

No changes in fibrinogen levels were detected 6 hours after turpentine injection. Elevated fibrinogen levels were observed at 12 hours post injection, and reach a maximal level by 24 hours post injection.

Conclusions

Our results confirm the previously published findings (Kozak et al., American J. Physiology 272:2 R621, 1997; Kopf et.al., Nature 368:339–342, 1994), which suggest that IL-6 is an essential mediator of the acute-phase response to turpentine. The turpentine model can serve as a first-line in-vivo assay to determine the pharmacological efficacy of anti-IL-6 treatments.

PTR 5045 (SEQ ID NO:75) was tested in this model in compare to the non-relevant control peptide PTR 4041 (SEQ ID NO:33) (Lys-GlyC2-Leu-Ile-Gln-Leu-Phe-GlyN3-Lys-Lys-NH$_2$). The results are summarized in the following table 3.)

TABLE 3

The in-vivo effect of PTR 5045 on IL-6 mediated acute-phase response.

| | Mean weight loss | |
|---|---|---|
| | % | grams |
| PTR 4041 (control) | −7.3 | −2.51 |
| PTR 5045 | −3.93 | −1.35 |
| Student t-test | P = 0.035 | P = 0.047 |
| Mann-Whitney test | P = 0.029 | P = 0.023 |

Ten mice received 1 or 10 mg/kg of each peptide analog.

PTR 5045 reduces by about half the effect mediated by IL-6 on body weight during acute inflammation. The difference between PTR 5045 and the control peptide is significant also if taking only the 1 mg/kg dose.

Example 4

IL-6 Mediated Adjuvant Arthritis

The objective was to establish an in-vivo model of rheumatoid arthritis (RA), for testing the activity of Interleukin-6 (IL-6) inhibitors. The adjuvant arthritis model was chosen because it has clinical and pathological similarities to RA in humans, and based on the putative role that IL-6 plays in this inflammatory condition.

Rheumatoid arthritis is a chronic, multi-system autoimmune disease, mainly characterized by a persistent inflammatory synovitis, usually involving peripheral joints in a symmetric distribution. IL-6 has been implicated in RA, since increased levels were found in serum and synovial fluid of RA patients, and these levels were correlated with clinical parameters of inflammation (Miltenburg et al., British J. Rheumatology 30:186, 1991). Adjuvant induced arthritis in rats is used as a model for human RA because adjuvant arthritic animals develop the inflammatory and immunologic features which are observed in RA patients. Furthermore, IL-6 levels are elevated in the serum of arthritic rats, and the levels correlate with inflammation, and with the progress of the syndrome.

Method and Results

Genetically susceptible Lewis rats were used. The arthritis is induced by a single injection of complete Freund's adjuvant (CFA), containing heat killed Mycobacterium Tuberculosis in oil (10 mg/ml). The animals were injected intradermally at the base of the tail. The arthritis developed two weeks after immunization, and involved the small joints of the extremities. The rats were then subjected to a clinical scoring of the inflamed joints, and to a histo-pathological evaluation.

The rate of success in inducing arthritis is greater than 85%. Female rats are more susceptible than males.

Inflammation of the synovium, formation of pannus, erosion of cartilage and bone were all observed histopathologically, confirming the clinical severity.

Dexamethasone treatment completely abolished the clinical signs of arthritis, and can therefore be used as a positive control in this model. Delivery of the dexamethason treatment was successfully achieved by employing osmotic mini-pumps, which could also be used for the continuous administration of peptides.

Conclusions

Our results confirm the previously published descriptions of this RA model (Stanescu et al., Arthritis and Rheumatism 30:779, 1987).

The adjuvant arthritis model can serve as a disease model to determine the pharmacological activity of anti-IL-6 treatments. The testing is based on scoring of clinical parameters at the onset of the disease (day 12).

Example 5

Pancreatitis Induced by Taurocholic Acid

The objective is to establish an in-vivo model of acute pancreatitis for testing the activity of IL-6 inhibitors. The taurocholic acid induced pancreatitis model has clinical and pathological similarities to severe necrotizing acute pancreatitis.

In its severe form acute pancreatitis has clear systemic manifestations such as: circulatory failure, metabolic acidosis, ascites, hyperglycemia, hyperlipidemia, and ultimately a multisystem organ failure. IL-6 has been implicated in acute pancreatitis, since elevated serum levels were more predictive of disease severity or lethality as compared with C-reactive protein in patients with acute pancreatitis (Leser et al., Gastroenterology 101:782:5, 1991). Taurocholic acid induced pancreatitis in rats is used as a model for human pancreatitis because pancreatitis animals develop the biochemical and pathological features which are observed in pancreatitis patients. Furthermore, IL-6 levels were elevated in the serum of pancreatitis rats.

Method and Results

Male Wistar rats were used. The pancreatitis was induced by the infiltration of 0.5 ml of 10% sodium taurocholate, into several sites of the pancreatic parenchyma with a 30G needle. A progressive detergent effects took place, which resulted in a diffuse pancreatic necrosis, and a high mortality rate. The measured parameters were serum levels of the pancreatic enzymes amylase and lipase, serum IL-6, and mortality. In addition, a histopathological evaluation of the pancreas was performed.

A mortality rate of 60–80% was found in the pancreatitis animals, with no mortality in the sham control group. Severe hemorrhages and necrosis were evident in the pancreas, after taurocholate induction.

Fat necrosis throughout the peritoneal cavity, and marked intestinal dilation were found at 24 hours.

A significant elevation in serum IL-6 was observed at three hours, and reached its peak within 6 hours from the taurocholate injection.

A significant elevation of serum amylase was observed at two hours after pancreatitis induction.

Conclusions

Our results confirm the previously published findings, that IL-6 is elevated in animal models of pancreatitis.

The taurocholate induced pancreatitis model can serve as a disease model to determine the pharmacological activity of anti-IL-6 treatments.

The testing is be based on measuring levels of pancreatic enzymes in the serum, mortality, and histopathological scoring.

Example 6
Synthesis and in Vitro Activity of Further Preferred Backbone Cyclized IL-6 Antagonist PTRs Additional PTR analogs that were synthesized are listed in table 4, together with their respective chemical and biological data. Most of the peptides were synthesized during the initial phase of the research as part of the effort to discovery active peptides. The best $IC_{50}$ were observed using the B16F10.9 cell assay are around 10 µ/ml for PTR-5005 and around 20 µg/ml for PTR-5037. Of these two peptides, only PTR-5005 appears to be active on TF1 cells.

TABLE 4

Summary of synthesis and bioactivity of certain preferred PTRs (SEQ IDs NO:34 to NO:45).

| PTR | TF1 inhibition (100 µg/ml) | T1165 inhibition (100 µg/ml) | B16F10.9 inhibition (33 µg/ml) | Sequence |
|---|---|---|---|---|
| 5001 | 3 | 16 | 0 | Thr-GlyC3-Gln-Gly-Ala-Ala-Ile-Ile-GlyN3-Gln-Pro |
| 5003 | 20 | 32 | 36 | Tyr-Arg-Leu-Arg-Phe-GlyC3-Leu-Arg-Tyr-GlyN2 |
| 5005 | 98 | 132 | 37 | Tyr-Arg-Leu-Arg-Phe-GlyC3-Leu-Arg-Tyr-GlyN2 |
| 5007 | 6 | 13 | 0 | Tyr-Arg-Leu-Arg-Phe-GlyN2-Leu-Arg-GlyC3-Arg |
| 5009 | 8 | 24 | NT | GlyC3-Glu-Ser-Gln-Lys-GlyN3-Ala-Ala-Gln-Leu |
| 5011 | 11 | 23 | NT | Tyr-Arg-Leu-Ile-Phe-Glu-GlyN2-Arg-Tyr-GlyC2 |
| 5013 | 28 | 22 | NT | Tyr-Arg-Leu-Arg-Phe-Glu-GlyN2-Arg-Tyr-GlyC2 |
| 5015 | 21 | 19 | NT | Tyr-Arg-Leu-Arg-Phe-Glu-GlyN2-Arg-Tyr-GlyC2 |
| 5017 | 30 | NT | NT | Arg-Leu-Arg-Ala-Glu-GlyC2-Ser-Lys-GlyN3-Phe |
| 5019 | 14 | NT | NT | Asp-Leu-Gln-GlyN3-Ser-Leu-Arg-Ala-Leu-Arg-Gln |
| 5021 | 20 | NT | NT | Asp-Leu-Gln-GlyN2-Ser-Leu-Arg-Ala-Leu-Arg-Gln |
| 5023 | 11 | NT | NT | Asp-Leu-Gln-GlyN2-Ser-Leu-Arg-Ala-Leu-Arg-Gln |
| 5025 | 28 | NT | NT | Asp-Leu-Gln-GlyN2-Ser-Leu-Arg-Ala-Leu-Arg-Gln |
| 5027 | 56 | NT | NT | Tyr-Arg-Leu-Phe-Arg-GlyC3-Leu-Arg-Tyr-GlyN2 |
| 5029 | 36 | NT | NT | Tyr-Arg-Leu-Arg-Phe-Glu-GlyN2-Arg-Tyr-GlyC2 |
| 5031 | 20 | NT | NT | Tyr-Arg-Lys-Arg-Phe-GlyN2-Leu-Arg-GlyC3-Arg |
| 5033 | 20 | NT | NT | Tyr-Arg-Lys-Arg-Phe-GlyN2-Leu-Arg-GlyC3-Arg |
| 5035 | 2 | NT | NT | Tyr-Arg-GlyN2-Arg-Phe-Glu-Leu-Arg-GlyC3-Arg |
| 5037 | 1 | NT | NT | Tyr-Arg-Leu-Arg-Phe-AlaC3-Leu-Arg-Tyr-AlaN3-Ala-Glu |
| 5039 | −14 | NT | NT | Phe-Arg-Leu-Arg-Phe-AlaC3-Leu-Arg-Tyr-AlaN3 |

NT - Not Tested

Certain preferred analogs are described in table 5 and table 6.

TABLE 5

Certain preferred backbone cyclic peptide analogs capable of inhibition IL-6 derived from either IL-6, 4/29 IL-6R (SEQ IDs NO:45 to NO:47) or gp130.

| No. | Origin | Sequence | | | | | | | | |
|---|---|---|---|---|---|---|---|---|---|---|
| 01 | IL-6R | Tyr | Arg | Leu | Arg | Phe | GlyN2 | Leu | Arg | Tyr | GlyC3 |
| 02 | IL-6R | Tyr | Arg | Leu | Arg | Phe | GlyN2 | Leu | Arg | GlyC3 | Arg |
| 03 | IL-6R | Arg | Tyr | Arg | Ala | Glu | GlyC2 | Ser | Lys | GlyN3 | Phe |
| 04 | IL-6R | Ala | Glu | Arg | Ser | Lys | Thr | Phe | Thr | Thr | Trp |
| 05 | IL-6R | GlyN3 | Arg | GlyC3 | Lys | Thr | Phe | Thr | Thr | Trp | Met |
| 06 | IL-6R | Ala | GlyC2 | D/LArg | Phe | Lys | DThr | Phe | D/LThr | GlyN3 | D/LTrp |
| 07 | IL-6R | Ala | Val | Ala | Arg | GlyC2 | Pro | Arg | Trp | Leu | GlyN2 |
| 08 | IL-6R | Ala | Val | Pro | Glu | GlyC2 | Asp | Ser | GlyN2 | Phe | Ile |
| 08 | IL-6R | Ala | Val | Pro | Glu | GlyC2 | Asp | Ser | GlyN2 | Tyr | Ile |
| 09 | IL-6R | Glu | Gly | GlyC2 | Ser | Ser | Phe | Tyr | GlyN2 | Val | Ser |
| 10 | IL-6R | Tyr | Ile | Val | Ser | GlyC2 | Ala | Val | Ala | Ser | GlyN2 |
| 11 | IL-6R | GlyC2 | Met | Ala | Val | Ala | Ser | Ser | Val | Gly | GlyN2 |
| 12 | IL-6R | Ala | Val | GlyC2 | Ser | Ser | Val | Gly | GlyN2 | Lys | Phe |
| 13 | IL-6R | Gly | Ala | GlyC2 | Ile | Leu | Gln | Pro | GlyN2 | Pro | Pro |
| 14 | IL-6R | GlyC2 | Gln | Pro | Asp | Pro | Pro | Ala | GlyN2 | Ile | Thr |
| 15 | IL-6R | Ser | Gln | GlyC2 | Ser | Gln | Lys | Phe | Ser | Ala | GlyN2 |

TABLE 5-continued

Certain preferred backbone cyclic peptide analogs capable of inhibition IL-6 derived from either IL-6, 4/29 IL-6R (SEQ IDs NO:45 to NO:47) or gp130.

| No. | Origin | Sequence | | | | | | | | |
|-----|--------|------|------|------|------|------|------|------|------|------|
| 16 | IL-6 | GlyC2 | Asn | Leu | Pro | Lys | Met | Ala | Glu | Lys | GlyN2 |
| 17 | IL-6 | GlyC2 | Lys | Val | Leu | Ile | Gln | Phe | GlyN2 | Gln | Lys |
| 18 | gp130 | GlyC2 | Asn | Phe | Thr | Leu | Lys | Ser | GlyN2 | Trp | Ala |
| 19 | gp130 | Phe | Ala | Asp | Ala | GlyC2 | Ala | Lys | Arg | Asp | GlyN2 |
| 20 | gp130 | GlyC2 | Thr | Pro | Thr | Ser | Ala | Thr | GlyN2 | Asp | Tyr |
| 21 | gp130 | Asn | Phe | Asp | Pro | GlyC2 | Tyr | Lys | Val | Lys | GlyN2 |
| 22 | gp130 | Asn | Pro | GlyC2 | His | Asn | Leu | Ser | Val | Ile | GlyN2 |
| 23 | gp130 | Ser | Ile | GlyC2 | Lys | Leu | Thr | Trp | Thr | Asn | GlyN2 |
| 24 | gp130 | Tyr | Arg | GlyC2 | Lys | Asp | Ala | Ser | GlyN2 | Trp | Ser |
| 25 | gp130 | Arg | Thr | Lys | Asp | Ala | Ser | GlyC2 | Trp | Ser | GlyN2 |
| 26 | gp130 | GlyC2 | Ile | Pro | Pro | Glu | Asp | Thr | Ala | Ser | GlyN2 |
| 27 | gp130 | GlyC2 | Asp | Thr | Ala | Ser | Thr | Arg | Ser | Ser | GlyN2 |
| 28 | gp130 | GlyC2 | Ala | Ser | GlyN2 | Arg | Ser | Ser | Phe | Thr | Val |
| 29 | gp130 | Ser | Phe | GlyC2 | Val | Gln | Asp | Leu | Lys | Pro | GlyN2 |
| 30 | gp130 | Tyr | Val | Phe | Arg | Ile | Arg | GlyC2 | Met | Lys | GlyN2 |

The average activity of the peptides found following the above procedure is estimated to be over 100 µM as estimated from the results of the MPS experiments.

TABLE 6

Summary of activity of certain preferred analogs derived from the IL-6R (SEQ IDs NO:77 to NO:82).

| Sequence | | | | | | | | | | TF1 | B16F10.9 active at |
|------|------|------|------|------|------|------|------|------|------|-----|------|
| Lys | Arg | Lys | (D) Arg | Phe | AlaC3 | Leu | Arg | BTyr | AlaN3 | 85 | <12 uM |
| Trp | Arg | Lys | (D) Arg | Phe | AlaC3 | Leu | Arg | BTyr | AlaN3 | 32 | <12 uM |
| Trp | Arg | Lys | (D) Arg | (D) Phe | AlaC3 | Leu | Arg | BTyr | AlaN3 | 41 | <12 uM |
| (D) Lys | Arg | (D) Leu | (D) Arg | (D) Phe | AlaC3 | (D) Leu | Arg | (D) Tyr | AlaN3 | 92 | 47 uM |
| (D) Lys | Arg | Lys | Arg | (D) Phe | AlaC3 | Lys | Arg | Tyr | AlaN3 | 55 | 62 uM |
| (D) Lys | Arg | Lys | (D) Arg | (D) Phe | AlaC3 | Leu | Arg | Tyr | AlaN3 | 13 | 62 uM |
| Tyr | Arg | Lys | (D) Arg | (D) Phe | AlaC3 | Leu | (D) Arg | BTyr | AlaN3 | 19 | 47 uM |
| Lys | Arg | Lys | Arg | Phe | AlaC3 | Lys | (D) Arg | BTyr | AlaN3 | 21 | 62 uM |
| (D) Lys | Arg | Lys | (D) Arg | Phe | AlaC3 | (D) Leu | Arg | Tyr | AlaN3 | 3 | 62 uM |
| Lys | Arg | Leu | (D) Arg | (D) Phe | AlaC3 | Lys | Arg | BTyr | AlaN3 | 22 | not active |
| (D) Lys | Arg | Lys | Arg | Phe | AlaC3 | Leu | Arg | (D) Tyr | AlaN3 | 25 | not active |
| (D) Lys | Arg | Lys | Arg | (D) Phe | AlaC3 | Leu | Arg | (D) Tyr | AlaN3 | 23 | 62 uM |
| (D) Lys | Arg | Lys | Arg | (D) Phe | AlaC3 | Lys | (D) Arg | (D) Tyr | AlaN3 | 17 | 62 uM |
| (D) Lys | Arg | Lys | (D) Arg | (D) Phe | AlaC3 | Lys | Arg | Tyr | AlaN3 | 17 | 62 uM |
| (D) Lys | Arg | Lys | Arg | Phe | AlaC3 | Lys | Arg | (D) Tyr | AlaN3 | 21 | not active |
| (D) Lys | Arg | Lys | Arg | Phe | AlaC3 | Leu | (D) Arg | (D) Tyr | AlaN3 | 19 | not active |
| (D) Lys | Arg | Lys | Arg | Phe | AlaC3 | (D) Leu | (D) Arg | Tyr | AlaN3 | 27 | not active |
| (D) Tyr | Arg | Lys | Arg | Phe | AlaC3 | Lys | (D) Arg | (D) Tyr | AlaN3 | 22 | not active |

BTyr is a mixture of DTyr and LTyr, and thus these wells contain 2 peptides each.

The results in table 6 demonstrate a general agreement between the results of both types of bioassays. Most of the peptides tested which were positive on TF1 cells, were also positive on B16F10.9 cells.

The best peptide analogs obtained appear to inhibit the effect of IL-6 on B16F10.9 cells at theoretical crude concentrations below 12 uM, suggested $IC_{50}$ values close to 1 uM. Somewhat higher $IC_{50}$ values are observed in the TF1 assay.

Example 7
Design, Synthesis, Screening and Identification of Additional Preferred Backbone Cyclized Analogs Derived from the IL-6 Molecule Based on the crystal structure of IL-6 and experiments that correlate specific point mutations and IL-6 biological activity, crucial contact points in loop AB and helix D of the IL-6 molecule were determined (Xu et al. *J. Mol. Biol.*, 268: 468, 1997, and Simpson et al. Protein Sci. 6:929, 1997 and references cited there).

Applying the methods for identifying pharmacophore containing molecules from a virtual library (as disclosed in international patent application PCT IL/00/00218), a set of molecules that contained the pharmacophore and mimic the corresponding region of IL-6 protein were obtained. Those molecules were used for the design of combinatorial libraries of $10^7$ different backbone cyclic molecules. The synthesis of one example of these libraries (ab0373) is described in the following scheme:

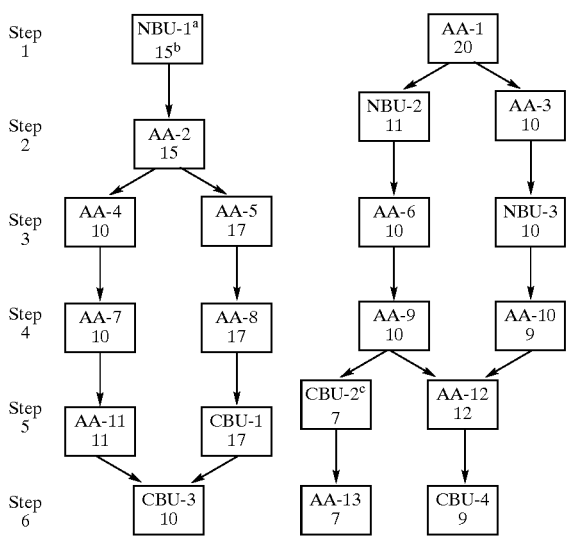

Wherein:
[a] NBU represents a building unit with amine reactive group
[b] The number in the second line of each step represent the number of individual amino acids coupled in each split arm.
[c] CBU represents a building unit with carboxyl reactive group.

The libraries were screened for binding of soluble IL-6. The information obtained was used for synthesis of backbone cyclic peptides in MPS format. Analyses for biological activity were performed on the TF1 human cell line.

Figure 4:
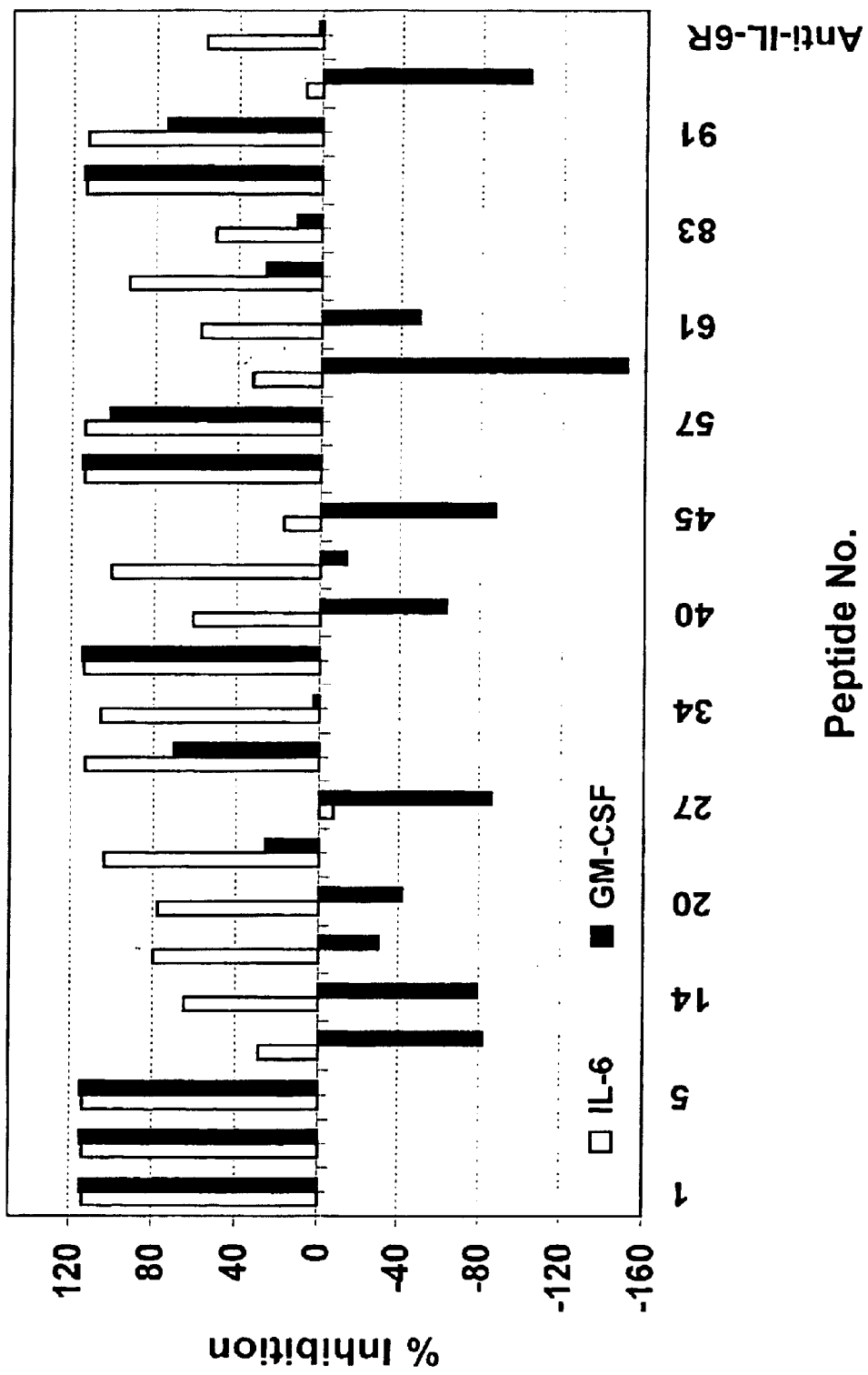
FIG. 4 is a chart describing the biological activity and selectivity of backbone cyclized peptide antagonists of IL-6, in TF1 cells maintained with IL-6 or GM-CSF.

Eighteen backbone cyclic peptides from the first MPS plate exhibit more then 45% inhibition at 1:10 dilution. Since the endpoint of the bioassay used is cell death, there is a need to check the specificity of the killing action, and to examine whether the cell death is due to inhibition of the IL-6 signaling pathway. The peptide analogs were therefore analyzed for their ability to induce non-specific cell death when the same cells were maintained with GM-CSF (instead of IL-6) as growth factor. The results of few of such activity and selectivity assays are summarized in Table 7 and FIG. 4. Some of the analogs exhibits non-specific inhibition (for example peptide 1,2 and 5 in table 7 and FIG. 4) but some (i.e. peptide 34 and 41) were clearly specific to the IL-6 pathway.

TABLE 7

Activity and selectivity of selected backbone cyclized analogs as determined in TF1 cells bioassay.

| | Inhibition of IL-6 activity (%) | | | | | |
|---|---|---|---|---|---|---|
| | Experiment 23 | | Experiment 24 | | | |
| Peptide | WST | | WST | | $^3$H-T | |
| Number | a | b | IL-6 | GM-CSF | IL-6 | GM-CSF |
| 1 | 122 | 112 | 124 | 111 | 114 | 115 |
| 2 | 117 | 109 | 112 | 107 | 114 | 115 |
| 5 | 122 | 113 | 130 | 109 | 114 | 115 |
| 8 | 9 | 6 | 15 | −36 | 29 | −82 |
| 14 | 40 | 47 | 50 | −41 | 65 | −79 |
| 17 | 50 | 44 | 67 | −23 | 80 | −30 |
| 20 | 37 | 56 | 49 | −59 | 78 | −42 |
| 25 | 54 | 54 | 77 | −49 | 104 | 26 |
| 27 | −55 | −186 | −28 | −64 | −7 | −86 |
| 33 | 116 | 119 | 112 | 39 | 113 | 70 |
| 34 | 97 | 108 | 96 | −27 | 106 | 3 |
| 35 | 119 | 118 | 106 | 110 | 114 | 115 |
| 40 | 42 | 72 | 43 | −45 | 61 | −63 |
| 41 | 96 | 100 | 95 | 25 | 101 | −13 |
| 45 | −53 | −144 | −23 | −39 | 18 | −87 |
| 50 | 115 | 111 | 103 | 107 | 114 | 115 |
| 57 | 122 | 114 | 121 | 48 | 114 | 102 |
| 60 | −1 | 2 | 11 | −93 | 33 | −151 |
| 61 | 54 | 58 | 86 | 4 | 58 | −49 |
| 81 | 38 | 46 | 92 | 43 | 93 | 27 |
| 83 | 2 | 4 | 31 | −5 | 51 | 12 |
| 88 | 96 | 98 | 112 | 103 | 114 | 115 |
| 91 | 98 | 106 | 123 | 45 | 113 | 75 |
| 92 | −108 | −152 | −25 | −79 | 8 | −103 |
| Anti IL-6R[a] | 38 | 39 | 42 | 10 | 56 | 2 |

[a] Anti IL-6R antibody in concentration of 1.35 ug/ml used as positive control in the assays.

What is claimed is:

1. A backbone cyclized peptide analog having IL-6 antagonist activity, having the general formula 3:

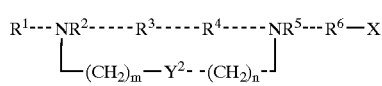

Formula No. 3 wherein m and n are 1 to 5;

X designates a terminal carboxy acid, amide or alcohol group;

$R^1$ is (D)Bip, Gln, Lys, Lys(ZCL) or Dab;

$R^2$ is (D)Lys, Gly, Ala or Trp $R^3$ is Orn, 4PyrAla, (L) or (D)Dab, (D)Arg, Lys or Dpr;

$R^4$ is Lys, Lys(ZCL), Arg, Arg(Mtr) or (D)Glu;

$R^5$ is Asn, Trp or (D)Ala;

$R^6$ is Arg, (p-NO$_2$)Phe, (L) or (D)Trp, Gln, Abu or Glu; and $Y^2$ is amide, thioether, thioester or disulfide.

2. A pharmaceutical composition comprising a backbone cyclized IL6 antagonist wherein the IL-6 antagonist has the general formula 3:

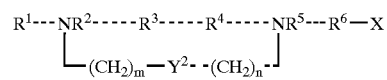

Formula No. 3 wherein m and n are 1 to 5;

X designates a terminal carboxy acid, amide or alcohol group;

$R^1$ is (D)Bip, Gln, Lys, Lys(ZCL) or Dab;

$R^2$ is (D)Lys, Gly, Ala or Trp $R^3$ is Orn, 4PyrAla, (L) or (D)Dab, (D)Arg, Lys or Dpr;

$R^4$ is Lys, Lys(ZCL), Arg, Arg(Mtr) or (D)Glu;

$R^5$ is Asn, Trp or (D)Ala;

$R^6$ is Arg, (p-NO2)Phe, (L) or (D)Trp, Gln, Abu or Glu; and $Y^2$ is amide, thioether, thioester or disulfide.

* * * * *